US006169206B1

(12) United States Patent
Kimura et al.

(10) Patent No.: US 6,169,206 B1
(45) Date of Patent: Jan. 2, 2001

(54) 4-(N,N-DIALKYLAMINO)ANILINE COMPOUND, PHOTOGRAPHIC PROCESSING COMPOSITION CONTAINING THE SAME AND COLOR IMAGE-FORMING METHOD

(75) Inventors: Keizo Kimura; Shigeo Hirano; Hiroshi Kawamoto, all of Minami-Ashigara (JP)

(73) Assignee: Fuji Photo Film Co., Ltd., Minami-Ashigara (JP)

( * ) Notice: Under 35 U.S.C. 154(b), the term of this patent shall be extended for 0 days.

(21) Appl. No.: 09/490,112

(22) Filed: Jan. 24, 2000

Related U.S. Application Data

(62) Division of application No. 09/148,165, filed on Sep. 4, 1998, now Pat. No. 6,043,006.

(30) Foreign Application Priority Data

Sep. 4, 1997 (JP) .................................................. 9-239894

(51) Int. Cl.[7] .................................................. C07C 215/00

(52) U.S. Cl. .......................... 564/443; 564/430; 564/441; 564/223; 564/50; 564/79; 564/440; 549/491; 549/475; 549/409; 549/57; 558/418; 562/58; 562/452; 560/29; 560/32; 546/136; 546/300; 548/530; 548/511; 544/59; 430/467

(58) Field of Search ............................ 430/467; 564/443, 564/430, 441, 223, 50, 79, 440; 549/491, 475, 469, 57; 558/418; 562/58, 452; 560/29, 32; 546/300, 136; 556/424; 548/530, 511; 544/59

(56) References Cited

U.S. PATENT DOCUMENTS

| | | |
|---|---|---|
| 5,721,093 | 2/1998 | Kimura et al. . |

FOREIGN PATENT DOCUMENTS

| | | |
|---|---|---|
| 807625 | 11/1997 | (EP) . |
| 5-257248 | 10/1993 | (JP) . |
| 6-161061 | 6/1994 | (JP) . |
| 7-36162 | 2/1995 | (JP) . |

*Primary Examiner*—Samuel Barts
(74) *Attorney, Agent, or Firm*—Burns, Doane, Swecker & Mathis, LLP

(57) ABSTRACT

4-(N,N-Dialkylamino)aniline compounds of the following general formula (I):

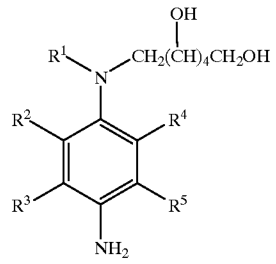

wherein $R^1$ represents an alkyl group, an aryl group or a heterocyclic group, $R^2$ to $R^5$ each represent a hydrogen atom or a substituent, and $R^2$ and $R^3$, $R^1$ and $R^2$, or $R^4$ and $R^5$ may form a ring together; a processing composition for color photography, which contains at least one of these compounds; and a color image-forming method wherein at least one of these aniline compounds is used.

10 Claims, No Drawings

4-(N,N-DIALKYLAMINO)ANILINE COMPOUND, PHOTOGRAPHIC PROCESSING COMPOSITION CONTAINING THE SAME AND COLOR IMAGE-FORMING METHOD

This application is a divisional of application Ser. No. 09/148,165, filed Sep. 4, 1998 now U.S. Pat. No. 6,043,006.

BACKGROUND OF THE INVENTION

The present invention relates to 4-(N,N-dialkylamino) aniline compounds. In particular, the present invention relates to new 4-(N,N-dialkylamino)aniline compounds useful as developing agents for silver halide color photography or as dyes or intermediates therefor.

4-(N,N-Dialkylamino)aniline compounds are useful as developing agents for silver halide color photography, and they are described in, for example, Japanese Patent Unexamined Published Application (hereinafter referred to as "J. P. KOKAI") Nos. Hei 5-257248, 6-161061 and 7-36162. 4-Aminoaniline, i.e. p-phenylenediamine, is useful as an intermediate for a dye for keratin fibers such as human hair.

SUMMARY OF THE INVENTION

The object of the present invention is to provide new 4-((N,N-dialkylamino)aniline compounds useful as developing agents having an excellent graininess for silver halide color photography, as dyes and intermediates therefor, particularly intermediates for dyes for keratin fibers such as human hair, as medicines and intermediates therefor, and agricultural chemicals and intermediates therefor.

The above-described object can be attained by the following compounds, composition and method (1) aniline compounds of the following general formula (I):

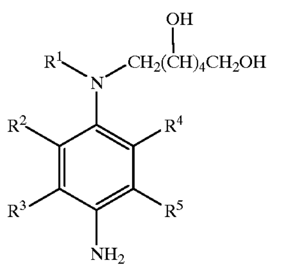

wherein $R^1$ represents an alkyl group, an aryl group or a heterocyclic group, $R^2$ to $R^5$ each represents a hydrogen atom or a substituent, and $R^2$ and $R^3$, $R^1$ and $R^2$, or $R^4$ and $R^5$ may form a ring together, (2) a processing composition for color photography, which contains at least one of the compounds set forth in above item (1), and (3) a color image-forming method wherein an image-exposed sensitive silver halide color photographic material is developed in the presence of at least one of the compounds set forth in above item (1).

4-(N,N-dialkylamino)aniline compounds having a saccharide group, i.e. 2,3,4,5,6-pentahydroxyhexyl group, as a 4-N substituent in the present invention are useful not only as color developing agents for silver halide color photography but also as intermediates for dyes for keratin fibers such as human hair, or as medicines and agricultural chemicals and intermediates for them.

DESCRIPTION OF THE PREFERRED EMBODIMENTS

The detailed description will be made on the general formula (I). $R^1$ represents an alkyl group, an aryl group or a heterocyclic group. Such a group may be substituted with a substituent such as an alkyl group, alkenyl group, alkynyl group, aryl group, hydroxyl group, nitro group, cyano group, or halogen atom or with another substituent comprising oxygen atom, nitrogen atom, sulfur atom and/or carbon atom. When $R^1$ is an alkyl group, it is preferred that, among the carbon atoms in $R^1$, the carbon atom directly bonded to the nitrogen atom in the general formula (I) is not bonded to an element other than hydrogen or carbon element. When $R^1$ is a heterocyclic group, it is preferred that a carbon atom constituting the heterocycle is connected with the nitrogen atom in the general formula (I). The alkyl groups may be linear, branched or cyclic alkyl groups having 1 to 25 carbon atoms, preferably 1 to 15 carbon atoms, such as methyl, ethyl, propyl, isopropyl, t-butyl, 2-hydroxyethyl, 3-hydroxypropyl, benzyl, 2-methanesulfonamidoethyl, 3-methanesulfonamidopropyl, 2-methanesulfonylethyl, 2-methoxylethyl, cyclopentyl, 2-acetamidoethyl, hydroxymethyl, 2-carboxyethyl, 2-carbamoylethyl, 3-carbamoylpropyl, 2,3-dihydroxypropyl, 3,4-dihydroxybutyl, 2,3,4-trihydroxybutyl, 2,3,4,5-tetrahydroxypentyl, methanesulfonamidomethyl, n-hexyl, n-octyl, n-decyl, n-octadecyl, 2-ethylhexyl, 2-hydroxypropyl, 4-hydroxybutyl, 2-carbamoylaminoethyl, 3-carbamoylaminopropyl, 4-carbamoylaminobutyl, 4-carbamoylbutyl, 2-carbamoyl-1-methylethyl, carbamoylaminomethyl, 4-nitrobutyl, 2-(2-hydroxyethoxy) ethyl, 2-[2-(2-hydroxyethoxy)ethoxy]ethyl, 2-(2-[2-(2-hydroxyethoxy)ethoxy]ethoxy)ethyl, 2-[2-(2-[2-(2-hydroxyethoxy) ethoxy]ethoxy)ethoxy]ethyl, 2-(2-[2-(2-[2-(2-hydroxyethoxy) ethoxy]ethoxy)ethoxy]ethoxy)ethyl, 2-[2-(2-(2-(2-[2-(2-hydroxyethoxy) ethoxy]ethoxy)ethoxy] ethoxy)ethoxy)ethyl, 2-(2-[2-(2-[2-(2-[2-(2-hydroxyethoxy) ethoxy]ethoxy)ethoxy]ethoxy)ethoxy]ethoxy)ethyl, 2-(2-methoxyethoxy)ethyl, 2-[2-(2-methoxyethoxy)ethoxy] ethyl, 2-(2-[2-(2-methoxyethoxy)ethoxy]ethoxy)ethyl, 2-[2-(2-[2-(2-methoxyethoxy) ethoxy]ethoxy)ethoxy]ethyl, 2-(2-ethoxyethoxy)ethyl and 2-[2-(2-butoxyethoxy)ethoxy]ethyl groups. In addition, the alkyl groups may be such as cyclohexyl, n-pentyl, n-heptyl, 2-[2-(2-phenyloxyethoxy) ethoxy]ethyl, n-butyl, n-nonyl, 2-(N,N-dimethylamino)ethyl and 2-mercaptoethyl groups.

The aryl groups may be those having 6 to 24 carbon atoms such as phenyl, naphthyl and p-methoxyphenyl groups. In addition, the aryl groups may be such as hydroxyphenyl, p-aminophenyl and N,N-diaminophenyl groups. The heterocyclic groups may be five-membered or six-membered, saturated or unsaturated heterocyclic groups containing 1 to 5 carbon atoms and at least one of oxygen, nitrogen and sulfur atoms. The number of the hetero atom constituting the ring may be one or more, and when the ring contains two or more elements of the hetero atoms, the kind of them may be the same or different. The heterocyclic groups include 2-furyl, 2-thienyl, 2-pyrimidinyl, 2-benzotriazolyl, imidazolyl and pyrazolyl groups.

$R^1$ is preferably an alkyl group or an aryl group, particularly the alkyl group.

Preferred examples of $R^1$ include methyl, ethyl, propyl, isopropyl, 2-hydroxyethyl, 3-hydroxypropyl, benzyl, 2-me thanesulfonamidoethyl, 2,3-dihydroxypropyl, 3,4-dihydroxybutyl, 2,3,4-trihydroxybutyl, 2,3,4,5-tetrahydroxypentyl, n-hexyl, n-octyl, n-decyl, n-octadecyl, 2-ethylhexyl, 2-hydroxypropyl, 4-hydroxybutyl, 2-(2-hydroxyethoxy)ethyl, 2-[2-(2-hydroxyethoxy)ethoxy]ethyl, 2-(2-[2-(2-hydroxyethoxy)ethoxy]ethoxy)ethyl, 2-[2-(2-[2-(2-hydroxyethoxy) ethoxy]ethoxy)ethoxy]ethyl, 2-(2-[2-(2-[2-(2-hydroxyethoxy) ethoxy]ethoxy)ethoxy]ethoxy)ethyl, 2-(2-methoxyethoxy)ethyl, 2-[2-(2-methoxyethoxy)ethoxy] ethyl, 2-[2-(2-butoxyethoxy)ethoxy]ethyl, phenyl and p-methoxyphenyl. Particularly preferred examples of $R^1$ include methyl, ethyl, propyl, isopropyl, 2-hydroxyethyl, 2,3-dihydroxypropyl, 3,4-dihydroxybutyl, n-hexyl, n-octyl, n-decyl, n-octadecyl, 2-ethylhexyl, 2-(2-hydroxyethoxy) ethyl, 2-[2-(2-hydroxyethoxy)ethoxy]ethyl, 2-(2-[2-(2-hydroxyethoxy)ethoxy]ethoxy)ethyl, 2-(2-methoxyethoxy) ethyl, 2-[2-(2-methoxyethoxy)ethoxy]ethyl, 2-[2-(2-butoxyethoxy)ethoxy]ethyl and phenyl.

$R^2$ to $R^5$ each represents a hydrogen atom or a substituent. Examples of the substituents include halogen atoms and groups such as alkyl, aryl, heterocyclic, cyano, nitro, hydroxyl, carboxyl, sulfo, alkoxyl, aryloxy, acylamino, amino, alkylamino, anilino, ureido, sulfamoylamino, alkylthio, arylthio, alkoxycarbonylamino, sulfonamido, carbamoyl, sulfamoyl, sulfonyl, alkoxycarbonyl, heterocyclic oxy, azo, acyloxy, carbamoyloxy, silyl, silyloxy, aryloxycarbonylamino, imido, heterocyclic thio, sulfinyl, phosphonyl, aryloxycarbonyl and acyl groups. Examples of the substituents also include mercapto and sulfino groups. They may be substituted with an alkyl group, alkenyl group, alkynyl group, aryl group, hydroxyl group, nitro group, cyano group, halogen atom or another substituent comprising oxygen atom, nitrogen atom, sulfur atom and/or carbon atom.

As for the detailed examples of substituents $R^2$ to $R^5$, the halogen atoms may be, for example, fluorine atom or chlorine atom. In addition, the halogen atoms may be bromine atom. The alkyl groups, aryl groups and heterocyclic groups may be those described above with reference to $R^1$.

The alkoxyl groups may be those having 1 to 16 carbon atoms, preferably 1 to 6 carbon atoms, such as methoxyl, ethoxyl, 2-methoxyethoxyl and 2-methanesulfonylethoxyl groups. The aryloxy groups may be those having 6 to 24 carbon atoms such as phenoxy, p-methoxyphenoxy and m-(3-hydroxypropionamido)phenoxy groups. The acylamino groups may be those having 1 to 16 carbon atoms, preferably 1 to 6 carbon atoms, such as acetamido, 2-methoxypropionamido and p-nitrobenzoylamido groups.

The alkylamino groups may be those having 1 to 16 carbon atoms, preferably 1 to 6 carbon atoms, such as dimethylamino, diethylamino and 2-hydroxyethylamino groups. The anilino groups may be those having 6 to 24 carbon atoms such as anilino, m-nitroanilino and N-methylanilino groups. The ureido groups may be those having 1 to 16 carbon atoms, preferably 1 to 6 carbon atoms, such as ureido, methylureido, N,N-diethylureido and 2-methanesulfonamidoethylureido groups.

The sulfamoylamino groups may be those having 0 to 16 carbon atoms, preferably 0 to 6 carbon atoms, such as dimethylsulfamoylamino, methylsulfamoylamino and 2-methoxyethylsulfamoylamino groups. The alkylthio groups may be those having 1 to 16 carbon atoms, preferably 1 to 6 carbon atoms, such as methylthio, ethylthio and 2-phenoxyethylthio groups. The arylthio groups may be those having 6 to 24 carbon atoms such as phenylthio, 2-carboxyphenylthio and 4-cyanophenylthio groups. The alkoxycarbonylamino groups may be those having 2 to 16 carbon atoms, preferably 2 to 6 carbon atoms, such as methoxycarbonylamino, ethoxycarbonylamino and 3-methanesulfonylpropoxycarbonylamino groups.

The sulfonamido groups may be those having 1 to 16 carbon atoms, preferably 1 to 6 carbon atoms, such as methanesulfonamido, p-toluenesulfonamido and 2-methoxyethanesulfonamido groups. The carbamoyl groups may be those having 1 to 16 carbon atoms, preferably 1 to 6 carbon atoms, such as carbamoyl, N,N-dimethylcarbamoyl and N-ethylcarbamoyl groups. The sulfamoyl groups may be those having 0 to 16 carbon atoms, preferably 0 to 6 carbon atoms, such as sulfamoyl, dimethylsulfamoyl and ethylsulfamoyl groups.

The sulfonyl groups may be aliphatic or aromatic sulfonyl groups having 1 to 16 carbon atoms, preferably 1 to 6 carbon atoms, such as methanesulfonyl, ethanesulfonyl and 2-chloroethanesulfonyl groups. The alkoxycarbonyl groups may be those having 1 to 16 carbon atoms, preferably 1 to 6 carbon atoms, such as methoxycarbonyl, ethoxycarbonyl and t-butoxycarbonyl groups. The heterocyclic oxy groups may be five-membered or six-membered, saturated or unsaturated heterocyclic oxy groups containing 1 to 5 carbon atoms and at least one of oxygen, nitrogen and sulfur atoms. The number of the hetero atom(s) constituting the ring may be one or more, and when the ring contains two or more elements of the hetero atoms, the kind of them may be the same or different. Examples of the heterocyclic oxy groups include 1-phenyltetrazolyl-5-oxy, 2-tetrahydropyranyloxy and 2-pyridyloxy groups.

The azo groups may be those having 1 to 16 carbon atoms, preferably 1 to 6 carbon atoms, such as phenylazo, 2-hydroxy-4-propanoylphenylazo and 4-sulfophenylazo groups. The acyloxy groups may be those having 1 to 16 carbon atoms, preferably 1 to 6 carbon atoms, such as acetoxy, benzoyloxy and 4-hydroxybutanoyloxy groups. The carbamoyloxy groups may be those having 1 to 16 carbon atoms, preferably 1 to 6 carbon atoms, such as N,N-dimethylcarbamoyloxy, N-methylcarbamoyloxy and N-phenylcarbamoyloxy groups.

The silyl groups may be those having 3 to 16 carbon atoms, preferably 3 to 6 carbon atoms, such as trimethylsilyl, isopropyldiethylsilyl and t-butyldimethylsilyl groups. The silyloxy groups may be those having 3 to 16 carbon atoms, preferably 3 to 6 carbon atoms, such as trimethylsilyloxy, triethylsilyloxy and diisopropylethylsilyloxy groups. The aryloxycarbonylamino groups may be those having 7 to 24 carbon atoms such as phenoxycarbonylamino, 4-cyanophenoxycarbonylamino and 2,6-dimethoxyphenoxycarbonylamino groups.

The imido groups may be those having 4 to 16 carbon atoms such as N-succinimido and N-phthalimido groups. The heterocyclic thio groups may be five-membered or six-membered, saturated or unsaturated heterocyclic thio groups containing 1 to 5 carbon atoms and at least one of oxygen, nitrogen and sulfur atoms. The number of the hetero atom(s) constituting the ring may be one or more, and when the ring contains two or more elements of the hetero atoms, the kind of them may be the same or different. Examples of the heterocyclic thio groups include 2-benzothiazolylthio and 2-pyridylthio groups.

The sulfinyl groups may be those having 1 to 16 carbon atoms, preferably 1 to 6 carbon atoms, such as methanesulfinyl, benzenesulfinyl and ethanesulfinyl groups. The phosphonyl groups may be those having 2 to 16 carbon atoms, preferably 2 to 6 carbon atoms, such as methoxyphosphonyl, ethoxyphosphonyl and phenoxyphosphonyl groups. The aryloxycarbonyl groups may be those having 7 to 24 carbon atoms such as phenoxycarbonyl, 2-methylphenoxycarbonyl and 4-acetamidophenoxycarbonyl groups. The acyl groups may be those having 1 to 16 carbon atoms, preferably 1 to 6 carbon atoms, such as acetyl, benzoyl and 4-chlorobenzoyl groups.

$R^2$ to $R^5$ are preferably hydrogen atom, alkyl groups, aryl groups, alkoxyl groups, acylamino groups, ureido groups, sulfamoylamino groups, sulfonylamino groups, carbamoyl groups or sulfamoyl groups. $R^2$ to $R^5$ are particularly preferably hydrogen atom, alkyl groups, alkoxyl groups, carbamoyl groups, sulfamoyl groups or ureido groups. They are still preferably hydrogen atom, alkyl groups and alkoxyl groups. $R^2$ and $R^4$ are particularly preferably hydrogen atom, alkyl groups or alkoxyl groups, and $R^5$ is particularly preferably alkyl groups or alkoxyl groups.

Preferred examples of $R^2$ to $R^5$ include hydrogen atom and methyl, ethyl, n-propyl, i-propyl, n-butyl, t-butyl, t-pentyl, di-t-octyl, hydroxymethyl, 1,3-dihydroxy-2-propyl, phenyl, m-hydroxyphenyl, methoxy, ethoxy, i-propoxy, 2-hydroxyethoxy, 2-methanesulfonylethoxy, 2-(2-hydroxyethoxy)ethoxy, 2-[2-(2-hydroxyethoxy) ethoxy]ethoxy), acetamido, 2-methoxypropionamido, p-hydroxybenzoylamido, ureido, methylureido, N,N-dimethylureido, 2-methanesulfonamidoethylureido, dimethylsulfamoylamino, methylsulfamoylamino, 2-methoxyethylsulfamoylamino, methanesulfonamido, p-toluenesulfonamido, 2-methoxyethanesulfonamido, carbamoyl, N,N-dimethylcarbamoyl, N-ethylcarbamoyl, sulfamoyl, dimethylsulfamoyl and ethylsulfamoyl groups. Particularly preferred examples of $R^2$ to $R^5$ are hydrogen atom and methyl, ethyl, n-propyl, i-propyl, t-butyl, methoxy, i-propoxy, acetamido, ureido, methylureido, N,N-dimethylureido, dimethylsulfamoylamino, methylsulfamoylamino, methanesulfonamido, carbamoyl, N,N-dimethylcarbamoyl, N-ethylcarbamoyl, sulfamoyl and dimethylsulfamoyl groups. Still preferred examples of $R^2$ to $R^5$ are hydrogen atom, and methyl, ethyl, i-propyl, methoxy and i-propoxy groups.

$R^2$ and $R^3$, $R^1$ and $R^2$, or $R^4$ and $R^5$ may form a ring, preferably a five-membered or six-membered ring together. It is preferred that the ring formed by $R^2$ and $R^3$, $R^1$ and $R^2$, or $R^4$ and $R^5$ is a five-membered or six-membered, saturated or unsaturated heterocyclic ring containing 1 to 5 carbon atoms and at least one of oxygen, nitrogen and sulfur atoms. It is still preferred that the ring is formed by $R^1$ and $R^2$ or $R^4$ and $R^5$. It is particularly preferred that $R^1$ and $R^2$ form a substituted or unsubstituted ethylene chain or a substituted or unsubstituted trimethylene chain together. It is also particularly preferred that $R^4$ and $R^5$ connect each other by way of an oxygen or nitrogen atom to form a furan or pyrrole ring. The substituents may be those described above with reference to $R^2$ to $R^5$. Preferred substituents include halogen atoms, and hydroxyl, alkyl, alkoxyl, carboxyl, acylamino, alkylamido, ureido, sulfamoylamino, akoxycarbonylamino, sulfonylamino, carbamoyl, sulfamoyl, sulfonyl, alkoxycarbonyl, acyloxy, carbamoyloxy and acyl groups. Particularly preferred substituents are hydroxyl, alkyl, carboxyl, acylamino, ureido, akoxycarbonylamino, sulfonylamino, carbamoyl, acyloxy and carbamoyloxy groups. Still preferred substituents are hydroxyl, alkyl and carboxyl groups. Examples of the ethylene chains and trimethylene chains formed by $R^1$ and $R^2$ include ethylene, 1-methylethylene (the carbon atom bonded to the nitrogen atom is in the 1-position), 2-methylethylene, 1,2-dimethylethylene, 1,1,2-trimethylethylene, 1,2,2-trimethylethylene, 1,1,2,2-tetramethylethylene, 2-hydroxymethylethylene, 2-hydroxyethylene, 1-methyl-2-hydroxyethylene, 1,1,2-trimethyl-2-carboxyethylene, 1,1,2,2-tetraethylethylene, trimethylene, 1,1-dimethyltrimethylene, 2,2-dimethyltrimethylene, 3,3-dimethyltrimethylene, 1,1,3-trimethyltrimethylene, 1,1,3-trimethyl-2-decyltrimethylene, 1,1,3-triethyl-2-methyltrimethylene, 1,1-diethyltrimethylene, 2,2-diethyltrimethylene, 3,3-diethyltrimethylene, 1,1,2,2,3,3-hexaethyltrimethylene, 1,1,3-trimethyl-3-carboxytrimethylene, 1,1,3-trimethyl-2-hydroxytrimethylene, 1,1-dimethyl-2-hydroxy-3-methylidenetrimethylene, 1,1,3-trimethyl-2,3-dihydroxytrimethylene, 1,1,3-trimethyl-2-aminotrimethylene, 1,1,3-trimethyl-2-dimethylaminotrimethylene, 1,1,3-trimethyl-2-bromotrimethylene, 1,1,3-trimethyl-2-(N-pyrazolyl) trimethylene, 1,1-dihydroxymethyl-3-methyltrimethylene, 1,1-dimethyl-3-hydroxymethyltrimethylene, 1,1-dimethyl-3-formyltrimethylene, 1,1-dimethyl-3-carboxytrimethylene, 1,1-dimethyl-3-carbamoyltrimethylene, 1,1-dimethyl-3-dimethylcarbamoyltrimethylene, 1,1-dimethyl-3-hydroxymethyl-2,3-dihydroxytrimethylene and 1,1-dimethyl-3-hydroxymethyl-2-hydroxytrimethylene. Among them, preferred ethylene chains and trimethylene chains are ethylene, 1-methylethylene, 2-methylethylene, 1,2-dimethylethylene, 1,2,2-trimethylethylene, 1,1,2,2-tetramethylethylene, 2-hydroxyethylene, 1-methyl-2-hydroxyethylene, 1,1-dimethyltrimethylene, 2,2-dimethyltrimethylene, 3,3-dimethyltrimethylene, 1,1,3-trimethyltrimethylene, 1,1,3-trimethyl-2-methyltrimethylene, 1,1,3-trimethyl-2-hydroxytrimethylene, 1,1,3-trimethyl-2,3-dihydroxytrimethylene, 1,1-dimethyl-3-hydroxymethyltrimethylene and 1,1-dimethyl-3-hydroxymethyl-2-hydroxytrimethylene. Particularly preferred examples of them are ethylene, 1-methylethylene, 2-methylethylene, 1,2-dimethylethylene, 1,1-dimethyltrimethylene, 2,2-dimethyltrimethylene, 3,3-dimethyltrimethylene, 1,1,3-trimethyltrimethylene, 1,1,3-trimethyl-2-hydroxytrimethylene and 1,1-dimethyl-3-hydroxymethyltrimethylene.

Particularly preferred compounds represented by the general formula (I) are those wherein $R^1$ is an alkyl group, $R^2$ and $R^4$ are hydrogen atom, alkyl groups or alkoxyl groups, $R^3$ is a hydrogen atom or a substituent and $R^5$ is alkyl groups or alkoxyl groups. Among them, those wherein $R^2$ is alkyl groups or alkoxyl groups, $R^4$ is hydrogen atom, alkyl groups or alkoxyl groups, and $R^1$ and $R^2$ may form a ring together, and those wherein $R^2$ is hydrogen atom, $R^4$ is alkyl groups or alkoxyl groups, and $R^4$ and $R^5$ may form a ring together are more preferred.

Still particularly preferred compounds represented by the general formula (I) are those wherein $R^1$ represents a linear, branched or cyclic alkyl group having 1 to 25 carbon atoms or aryl group having 6 to 24 carbon atoms, $R^2$ to $R^4$ each represents a hydrogen atom, and $R^5$ represents a hydrogen atom or a substituent selected from the group consisting of halogen atoms and a linear, branched or cyclic alkyl group having 1 to 25 carbon atoms, aryl group having 6 to 24 carbon atoms or five-membered or six-membered, saturated or unsaturated heterocyclic group containing 1 to 5 carbon atoms and at least one of oxygen, nitrogen and sulfur atoms, cyano, nitro, hydroxyl, carboxyl, sulfo, alkoxyl group having 1 to 16 carbon atoms, aryloxy group having 6 to 24 carbon atoms, acylamino group having 1 to 16 carbon atoms, amino, alkylamino group having 1 to 16 carbon atoms, anilino group having 6 to 24 carbon atoms, ureido group having 1 to 16 carbon atoms, sulfamoylamino group having 0 to 16 carbon atoms, alkylthio group having 1 to 16 carbon atoms, arylthio group having 6 to 24 carbon atoms, alkoxycarbonylamino group having 2 to 16 carbon atoms, sulfonamido group having 1 to 16 carbon atoms, carbamoyl group having 1 to 16 carbon atoms, sulfamoyl group having 0 to 16 carbon atoms, sulfonyl group having 1 to 16 carbon atoms, alkoxycarbonyl group having 1 to 16 carbon atoms, five-membered or six-membered, saturated or unsaturated heterocyclic oxy group containing 1 to 5 carbon atoms and at least one of oxygen, nitrogen and sulfur atoms, azo group having 1 to 16 carbon atoms, acyloxy group having 1 to 16 carbon atoms, carbamoyloxy group having 1 to 16 carbon atoms, silyl group having 3 to 16 carbon atoms, silyloxy group having 3 to 16 carbon atoms, aryloxycarbonylamino group having 7 to 24 carbon atoms, imido group having 4 to 16 carbon atoms, five-membered or six-membered, saturated or unsaturated heterocyclic thio group containing 1 to 5 carbon atoms and at least one of oxygen, nitrogen and sulfur atoms, sulfinyl group having 1 to 16 carbon atoms, phosphonyl group having 2 to 16 carbon atoms, aryloxycarbonyl group having 7 to 24 carbon atoms and acyl group having 1 to 16 carbon atoms, and $R^2$ and $R^3$, $R^1$ and $R^2$, or $R^4$ and $R^5$ may form a five-membered or six-membered, saturated or unsaturated heterocyclic ring containing 1 to 5 carbon atoms and at least one of oxygen, nitrogen and sulfur atoms together. Still more preferred compounds represented by the general formula (I) are those wherein $R^1$ represents a linear, branched or cyclic alkyl group having 1 to 25 carbon atoms or aryl group having 6 to 24 carbon atoms, $R^2$ to $R^4$ each represents a hydrogen atom, and $R^5$ represents a hydrogen atom or a substituent selected from the group consisting of a linear, branched or cyclic alkyl group having 1 to 25 carbon atoms, alkoxyl group having 1 to 16 carbon atoms, ureido group having 1 to 16 carbon atoms, carbamoyl group having 1 to 16 carbon atoms and sulfamoyl group having 0 to 16 carbon atoms, and $R^2$ and $R^3$, $R^1$ and $R^2$, or $R^4$ and $R^5$ may form a five-membered or six-membered, saturated or unsaturated heterocyclic ring containing 1 to 5 carbon atoms and at least one of oxygen, nitrogen and sulfur atoms together. Still further preferred compounds represented by the general formula (I) are those wherein $R^1$ represents an alkyl group having 1 to 15 carbon atoms, $R^2$ to $R^4$ each represents a hydrogen atom, and $R^5$ represents a hydrogen atom or an alkyl group having 1 to 25 carbon atoms, and $R^1$ and $R^2$ may form a substituted or unsubstituted ethylene chain or a substituted or unsubstituted trimethylene chain together.

Examples of the compounds represented by the general formula (I) of the present invention are given below, which by no means limit the invention. Although the stereostructure of the saccharide groups in the following formulae are not specified below, any possible stereostructure is possible.

D-1)

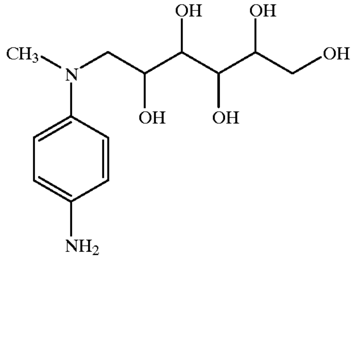

-continued

D-2)

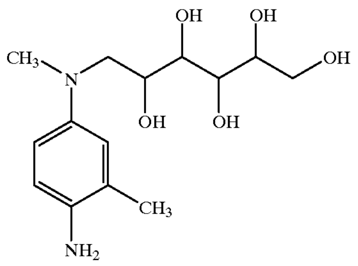

D-3)

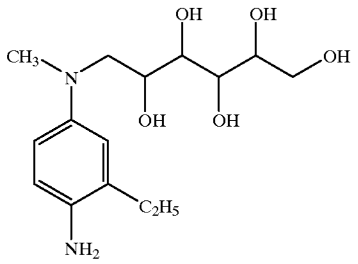

D-4)

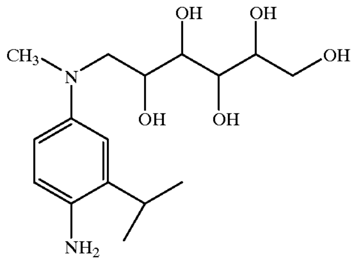

D-5)

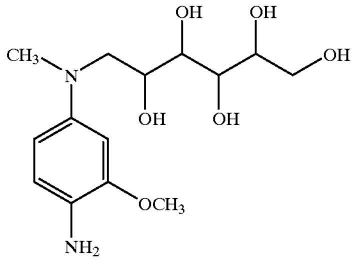

D-6)

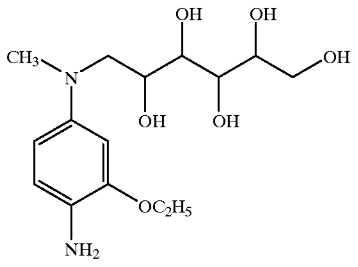

-continued
D-7)
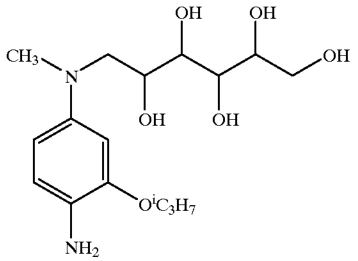
D-8)
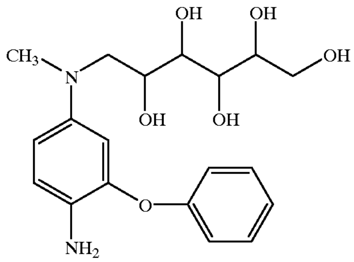
D-9)
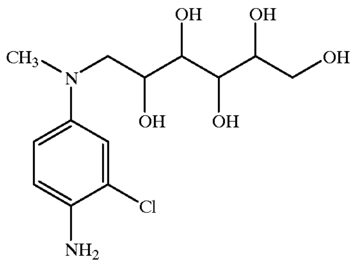
D-10)
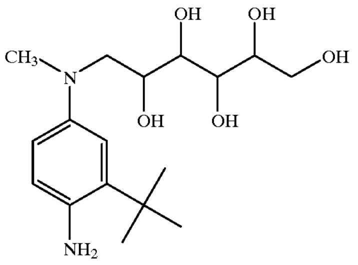
D-11)
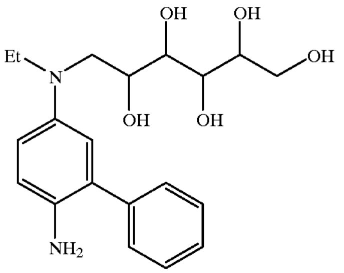
-continued
D-12)
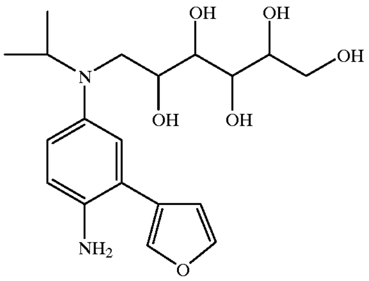
D-13)
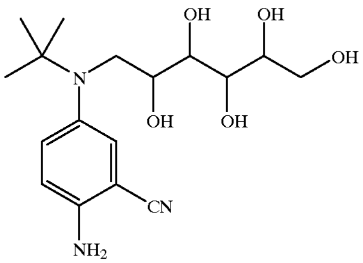
D-14)
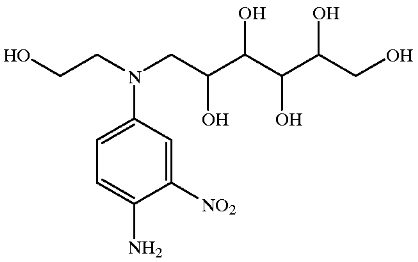
D-15)
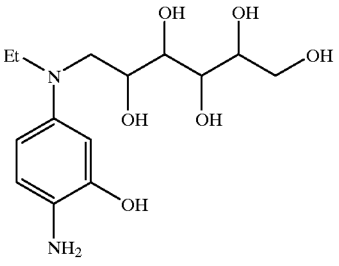
D-16)
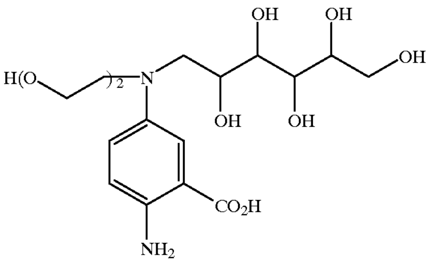

-continued
D-17)
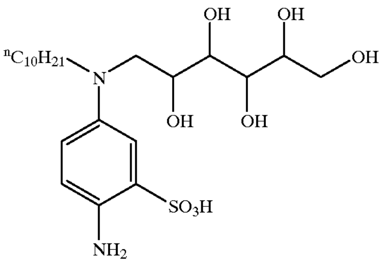
D-18)
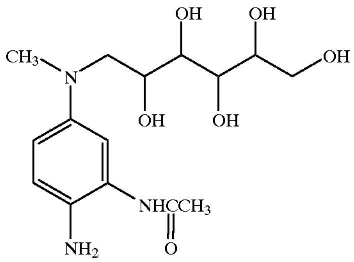
D-19)
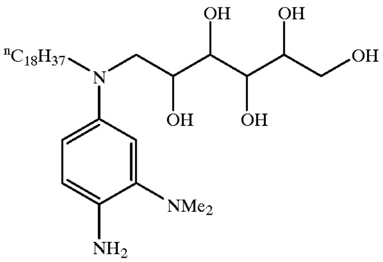
D-20)
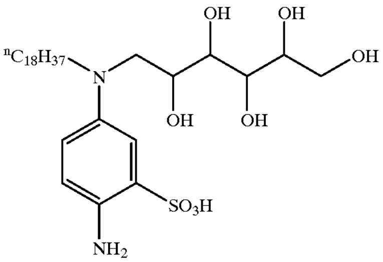
D-21)
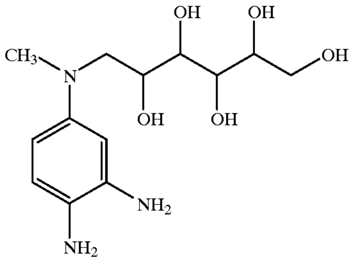
-continued
D-22)
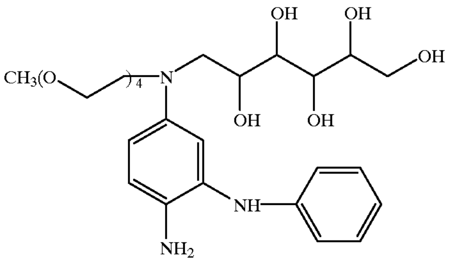
D-23)
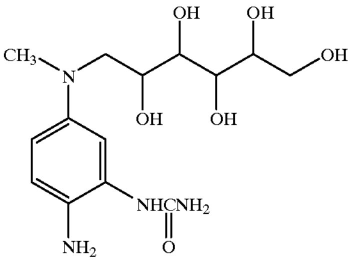
D-24)
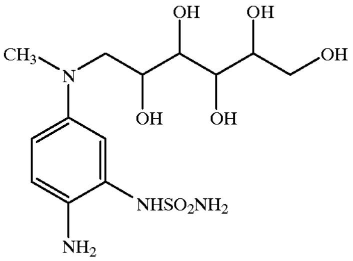
D-25)
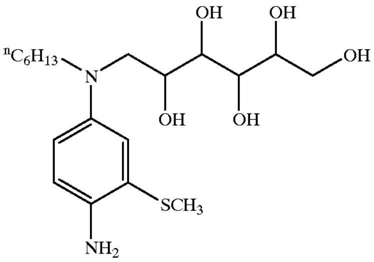
D-26)
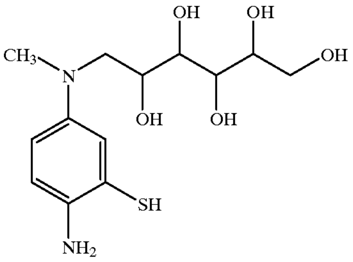

-continued
D-27)
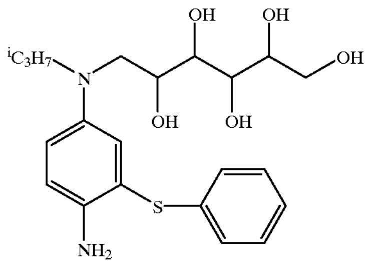
D-28)
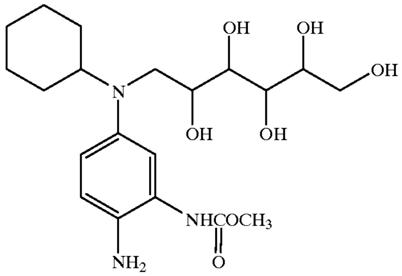
D-29)
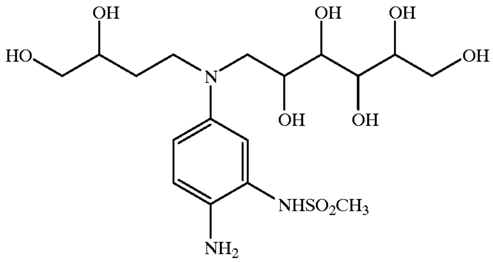
D-30)
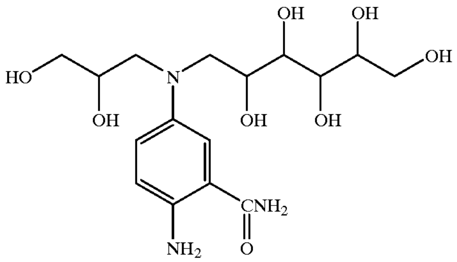
D-31)
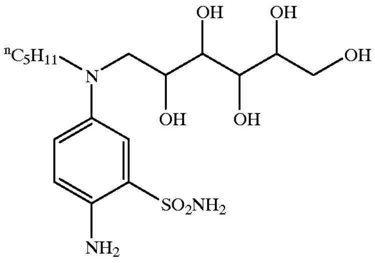
-continued
D-32)
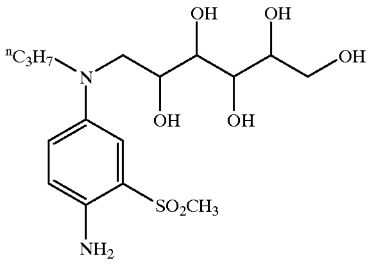
D-33)
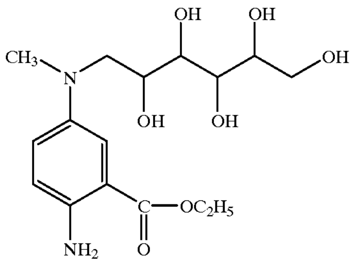
D-34)
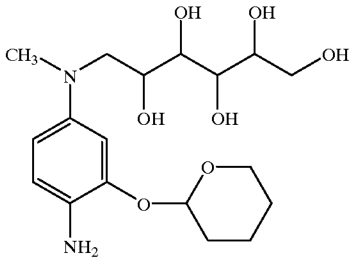
D-35)
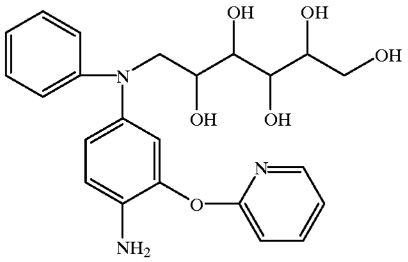
D-36)
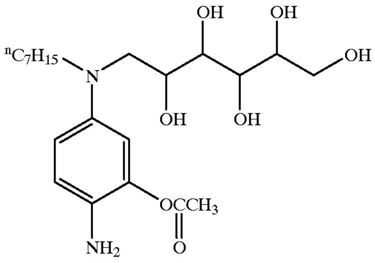

-continued
D-37)
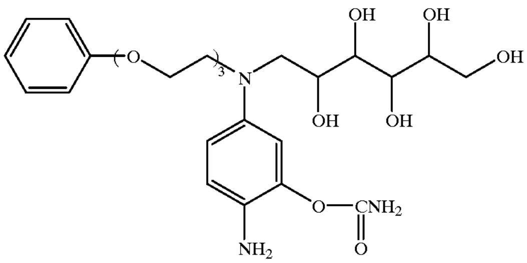
D-38)
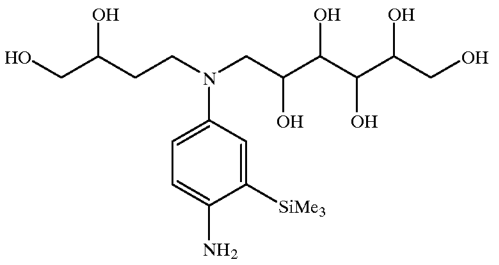
D-39)
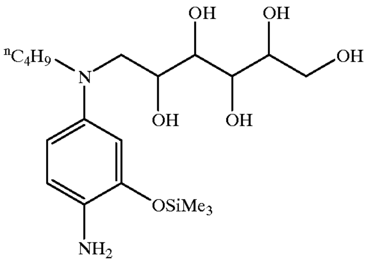
D-40)
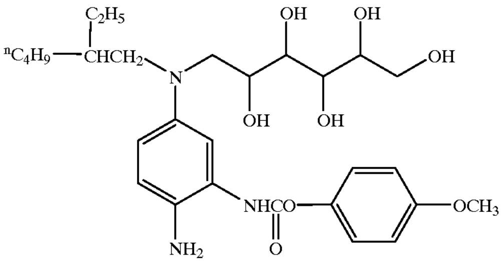
D-41)
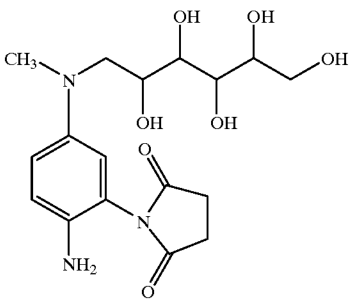
-continued
D-42)
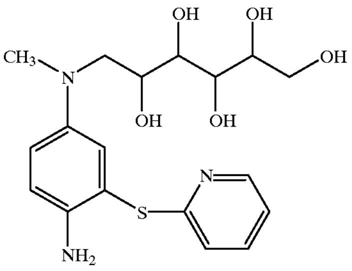
D-43)
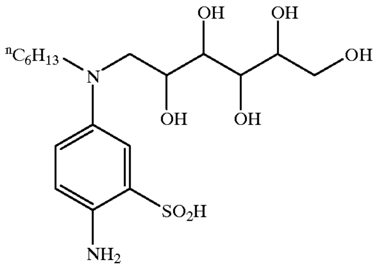
D-44)
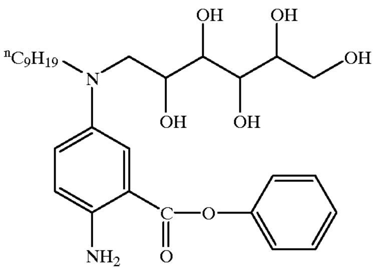
D-45)
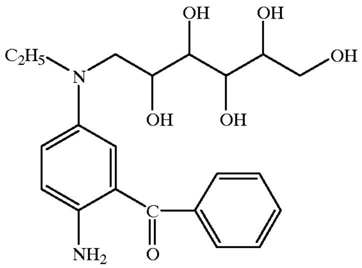
D-46)
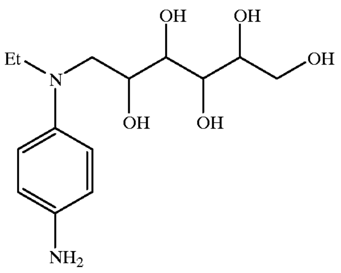

-continued
D-47)
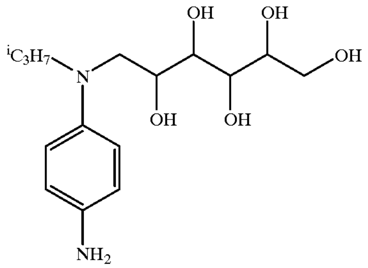
D-48)
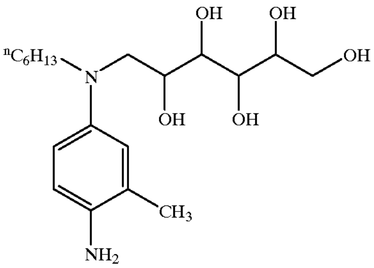
D-49)
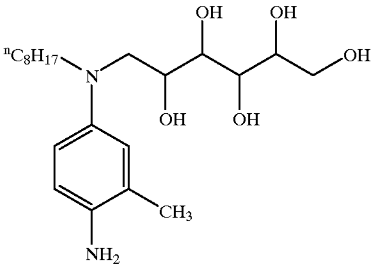
D-50)
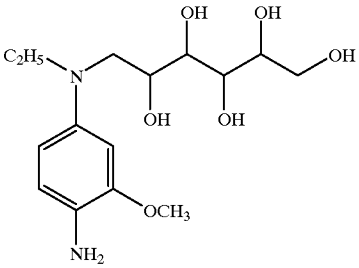
D-51)
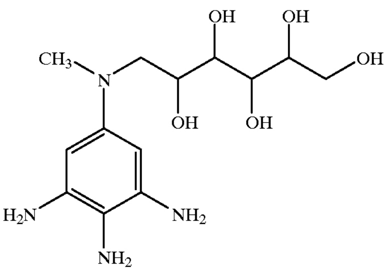
-continued
D-52)
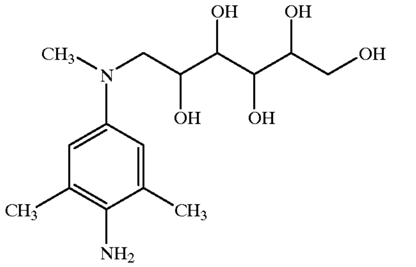
D-53)
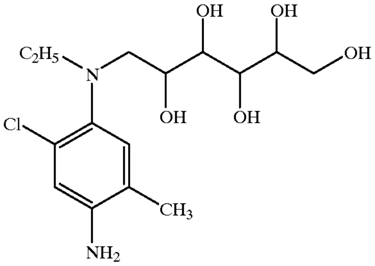
D-54)
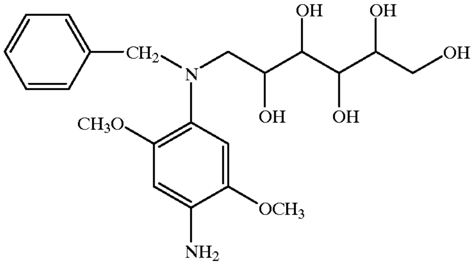
D-55)
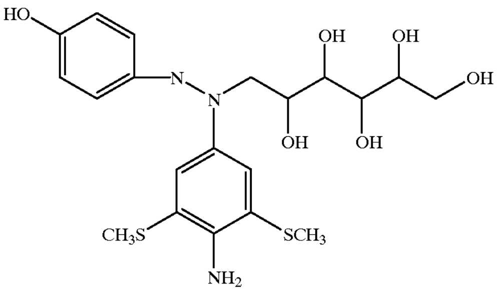
D-56)
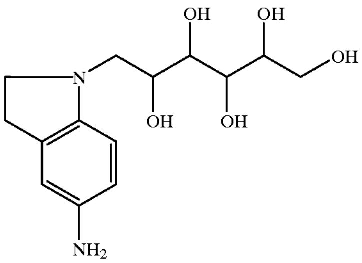

-continued
D-57)
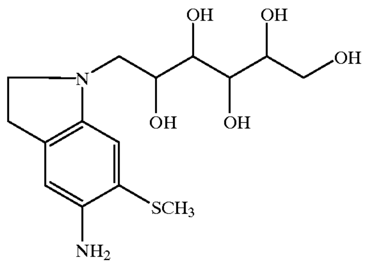
D-58)
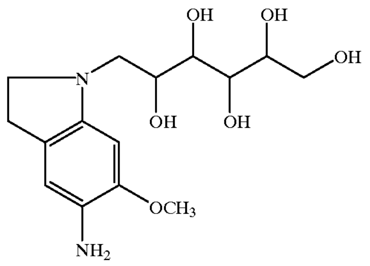
D-59)
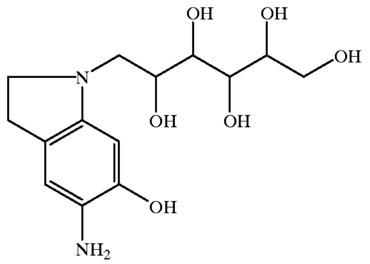
D-60)
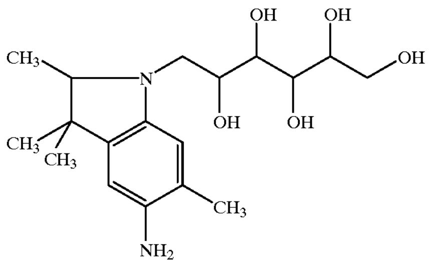
D-61)
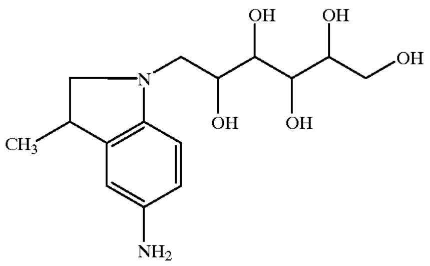
-continued
D-62)
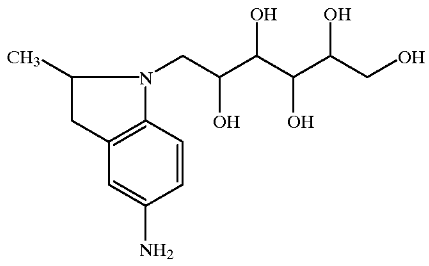
D-63)
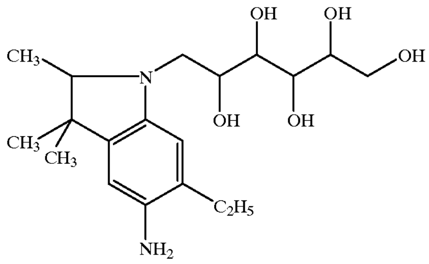
D-64)
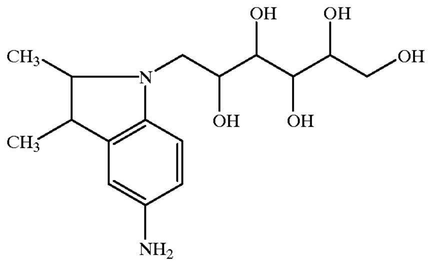
D-65)
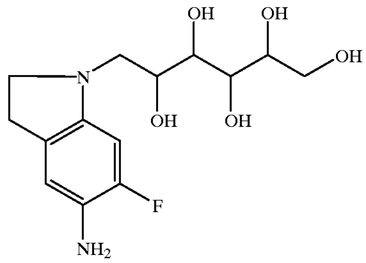
D-66)
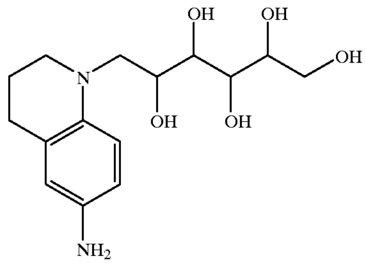

-continued
D-67)
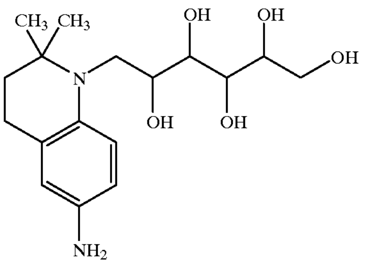
D-68)
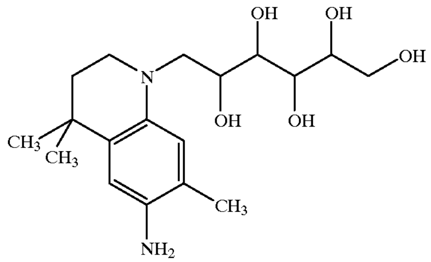
D-69)
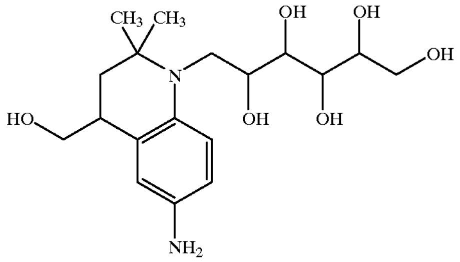
D-70)
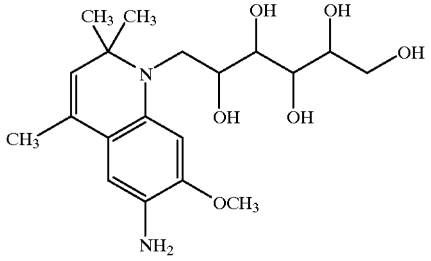
D-71)
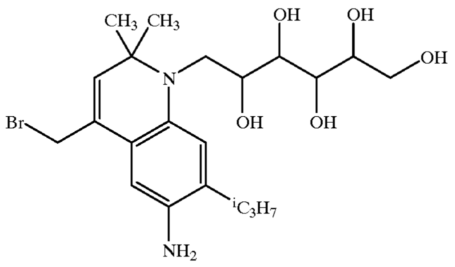
-continued
D-72)
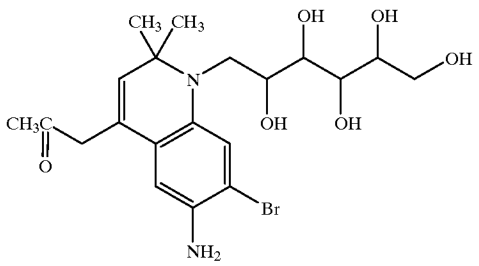
D-73)
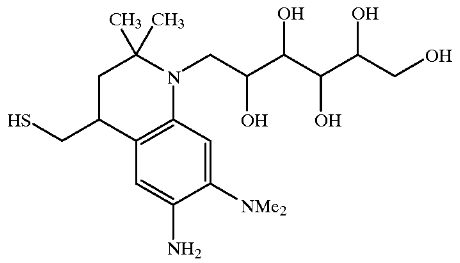
D-74)
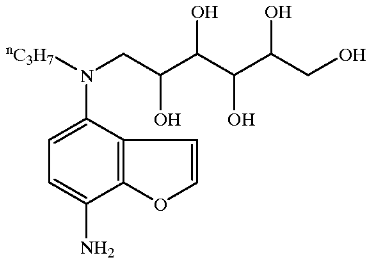
D-75)
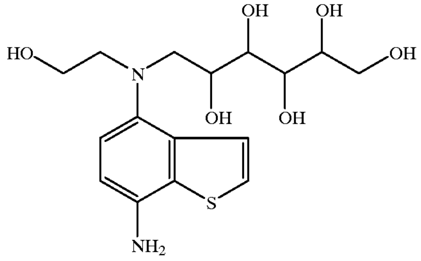
D-76)
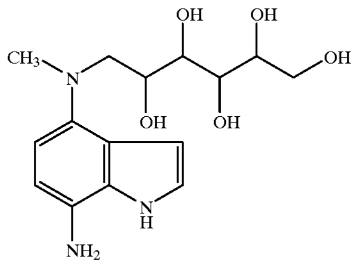

-continued
D-77)
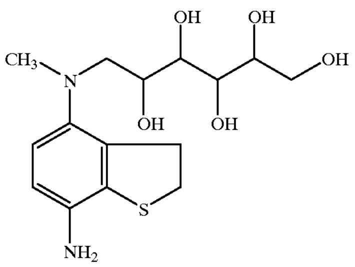
D-78)
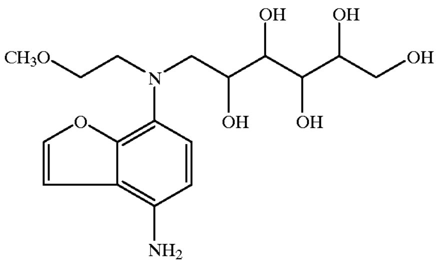
D-79)
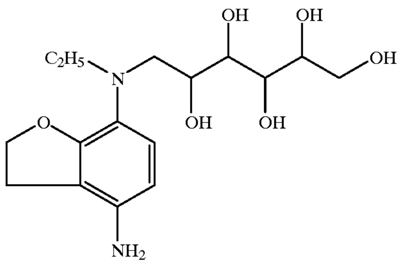
D-80)
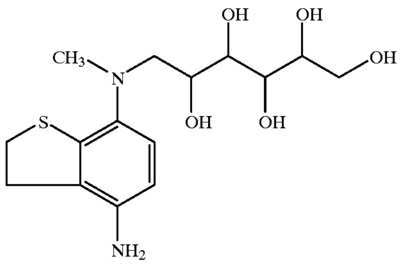
D-81)
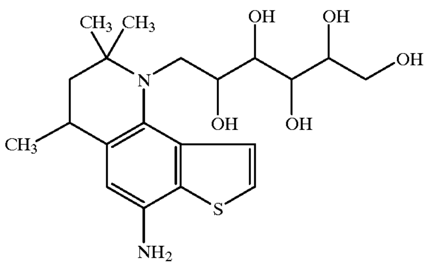
-continued
D-82)
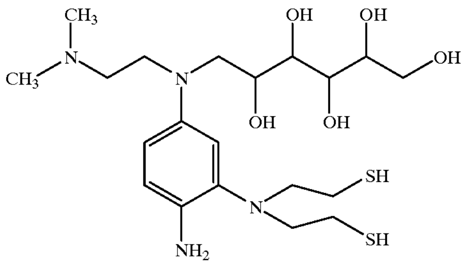
D-83)
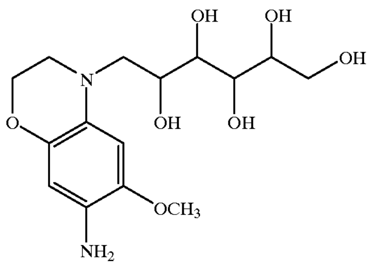
D-84)
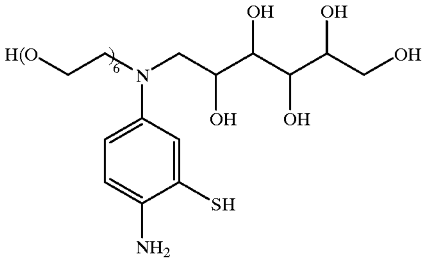
D-85)
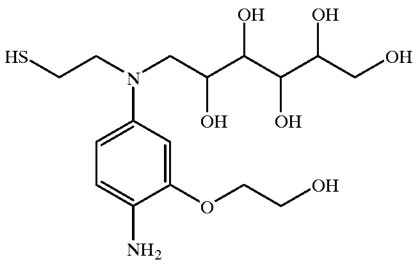
D-86)
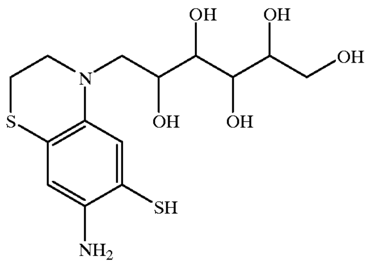

-continued

D-87)

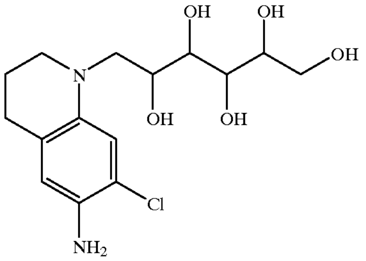

D-88)

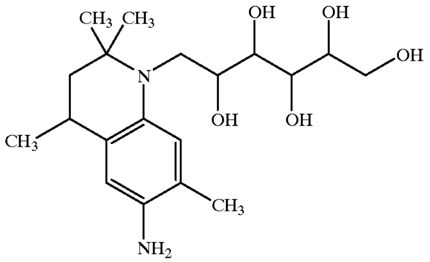

D-89)

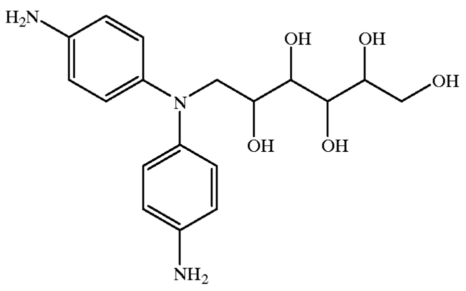

D-90)

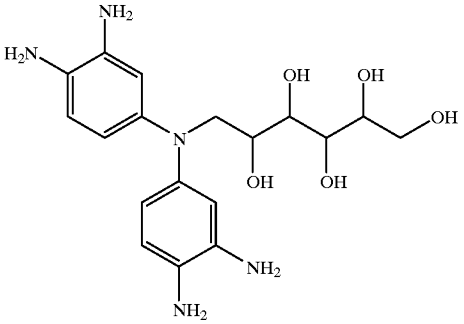

Since the compounds of the general formula (I) are very unstable when they are stored in the form of the free amines, it is preferred that they are produced and stored in the form of salts with an inorganic acid or an organic acid and converted into the free amines at the time of the use. Examples of the inorganic and organic acids used for forming the salts of the compounds of the general formula (I) include hydrochloric acid, sulfuric acid, phosphoric acid, p-toluenesulfonic acid, methanesulfonic acid and naphthalene-1,5-disulfonic acid. Among them, sulfuric acid and p-toluenesulfonic acid are preferred for forming the salts. The sulfates are the most desirable.

The description will be made on the use of the compounds of the present invention as color developing agents. Each of the compounds of the present invention is usable as the color developing agent either alone or in combination with other known p-phenylenediamine derivatives. Examples of typical compounds usable in combination with the compounds of the present invention are as follows, which by no means limit the invention: N,N-diethyl-p-phenylenediamine (P-1), 4-amino-3-methyl-N,N-diethylaniline (P-2), 4-amino-3-methyl-N-ethyl-N-(3-hydroxypropyl)aniline (P-3), 4-amino-N-ethyl-N-(2-hydroxyethyl)aniline (P-4), 4-amino-3-methyl-N-ethyl-N-(2-hydroxyethyl)aniline (P-5), 4-amino-3-methyl-N-ethyl-N-(2-methanesulfonamidoethyl)aniline (P-6), N-(2-amino-5-N,N-diethylaminophenylethyl)methanesulfonamide (P-7), N,N-dimethyl-p-phenylenediamine (P-8), 4-amino-3-methyl-N-ethyl-N-(2-methoxyethyl)aniline (P-9), 4-amino-3-methyl-N-ethyl-N-(4-hydroxybutyl)aniline (P-10) and 4-amino-3-methyl-N-ethyl-N-(2-butoxyethyl)aniline (P-11). Among the above-described p-phenylenediamine derivatives, the particularly preferred compound to be combined with the compounds of the present invention are P-3, P-5, P-6 or P-10. These p-phenylenediamine derivatives are usually used in the form of salts thereof such as sulfates, hydrochlorides, sulfites, p-toluenesulfonates, nitrates and naphthalene-1,5-disulfonates.

The processing composition may be in liquid form or solid form (such as powder, granules or tablets).

A combination of two or more of these compounds can be used depending on the purpose. The amount of the aromatic primary amine developing agent is preferably 0.001 to 0.2 mol, more preferably 0.005 to 0.1 mol, per liter of the color developer.

In the color development with the compound of the present invention, the compound may be incorporated into the processing solution or this compound or a precursor thereof is incorporated into the photosensitive material to form the compound in the developing process. The content of such a compound is 1 to 30 parts, preferably 1 to 10 parts and more preferably 1 to 4 parts, per part of the coupler.

The color developer may contain a compound for directly preserving the above-described aromatic primary amine color developing agent, which is selected from among hydroxylamines described in J.P. KOKAI Nos. Sho 63-5341, Sho 63-106655 and Hei 4-144446, hydroxamic acids described in J.P. KOKAI No. Sho 63-43138, hydrazines and hydrazides described in J.P. KOKAI No. Sho 63-146041, phenols described in J.P. KOKAI Nos. Sho 63-44657 and Sho 63-58443, α-hydroxyketones and α-aminoketones described in J.P. KOKAI No. Sho 63-44656, and saccharides described in J.P. KOKAI No. Sho 63-36244. Such a compound can be used in combination with monoamines described in J.P. KOKAI Nos. Sho 63-4235, 63-24254, 63-21647, 63-146040, 63-27841 and 63-25654, diamines described in J.P. KOKAI Nos. Sho 63-30845, 63-14640 and 63-43139, polyamines described in J.P. KOKAI Nos. Sho 63-21647, 63-26655 and 63-44655, nitroxyl radicals described in J.P. KOKAI No. Sho 63-53551, alcohols described in J.P. KOKAI Nos. Sho 63-43140 and 63-53549, oximes described in J.P. KOKAI No. Sho 63-56654 and tertiary amines described in J.P. KOKAI No. Sho 63-239447. The color developer may also contain, if necessary, a preservative such as metals described in J.P. KOKAI Nos. Sho 57-44148 and 57-53749, salicylic acids described in J.P. KOKAI No. Sho 59-180588, alkanolamines described in J.P. KOKAI No. Sho 54-3582, polyethyleneimines described in J.P. KOKAI No. Sho 56-94349 and aromatic polyhydroxyl compounds described in U.S. Pat. No. 3,746,544. Particularly when the hydroxylamines are used, they are preferably used in combination with the above-described alkanolamines or aromatic polyhydroxy compounds.

Particularly preferred preservatives are hydroxylamines represented by general formula (I) given in J.P. KOKAI No. Hei 3-144446. Among them, compounds having methyl, ethyl, sulfo or carboxyl group are preferred. The preservative is used in an amount of 20 to 200 mmol, preferably 30 to 150 mmol, per liter of the color developer.

The developer for the printing photosensitive material contains chlorine ion in an amount of preferably $3.0\times10^{-2}$ to $1.5\times10^{-1}$ mol/l, particularly preferably $3.5\times10^{-2}$ to $1.0\times10^{-1}$ mol/l. When the chlorine ion concentration is higher than the range of $1.5\times10^{-1}$ mol/l to $1.0\times10^{-1}$ mol/l, the development is retarded unfavorably. This is against the object of the present invention, i.e. to rapidly attain a high maximum density. When it is below $3.0\times10^{-2}$ mol/l, the fogging cannot be inhibited.

It is preferred in the present invention that the color developer contains $0.5\times10^{-5}$ to $1.0\times10^{-1}$ mol/l of bromine ion. The bromine ion concentration is more preferably $3.0\times10^{-5}$ to $5\times10^{-4}$ mol/l. When the bromine ion concentration is higher than $1\times10^{-3}$ mol/l, the development is retarded and the maximum density and sensitivity are lowered. When it is below $0.5\times10^{-5}$ mol/l, the fogging cannot be completely inhibited.

Chlorine ion and bromine ion may be directly added to the color developer, or they may be contained in the photosensitive material so that they are eluted into the color developer during the developing process.

When chlorine ion and bromine ion are to be directly added to the color developer, materials for feeding chlorine ion are sodium chloride, potassium chloride, ammonium chloride, lithium chloride, magnesium chloride and calcium chloride. Chlorine ion may be fed by a fluorescent brightening agent contained in the color developer. Materials for feeding bromine ion are sodium bromide, potassium bromide, ammonium bromide, lithium bromide, calcium bromide and magnesium bromide.

When chlorine ion and br6mine ion are eluted from the photosensitive material in the developing process, these ions may be fed by an emulsion or other materials.

The color developer can contain other additives described in J.P. KOKAI No. Hei 3-144446. For example, carbonates, phosphates, borates, hydroxybenzoates, etc. described on page 9 of that specification are usable as buffers for maintaining a predetermined pH. The color developer is kept at preferably pH 9.0 to 12.5, more preferably 9.5 to 11.5 with such a buffer.

Antifoggants include halide ions and organic antifoggants described on page 10 of that specification. Particularly when the concentration of the developing agent in the color developer is as high as at least 20 mmol/l or when the process is conducted at a temperature of as high as at least 40° C., the bromide ion concentration is preferably high to some extent. It is preferably 17 to 60 mmol/l. If necessary, the halogen can be removed with an ion exchange resin or an ion exchange membrane to control the halogen concentration in a preferred range.

As the chelating agents, aminopolycarboxylic acids, aminopolyphosphonic acids, alkylphosphonic acids and phosphonocarboxylic acids are preferably used. They are typified by ethyle nediaminetetraacetic acid, nitrilotriacetic acid, diethy lenetriaminepentaacetic acid, cyclohexanediaminetetraacetic acid, hydroxyethyliminodiacetic acid, 1-hydroxyethylidene-1,1-diphosphonic acid, nitrilo-N,N,N-trimethylenephosphonic acid, ethylenediamine-N,N,N,N-tetramethylenephosphonic acid, ethylenediamine-di(o-hydroxyphenylacetic acid) and salts of them. Preferred chelating agents include biodegradable compounds such as those described in J.P. KOKAI Nos. Sho 63-146998, Sho 63-199295, Sho 63-267750, Sho 63-267751, Hei 2-229146 and Hei 3-186841, German Patent No. 3,739,610 and European Patent No. 468,325.

If necessary, the color developer may further contain a development inhibitor selected from among benzimidazoles, benzothiazoles and mercapto compounds, a development accelerator selected from among benzyl alcohol, polyethylene glycols, quaternary ammonium salts and amines, a color-forming coupler, a competing coupler, an assistant developing agent such as 1-phenyl-3-pyrazolidone, a tackifier, and a surfactant selected from among alkylsulfonic acids, arylsulfonic acids, aliphatic carboxylic acids and aromatic carboxylic acids.

The color developer may contain a development accelerator, if necessary.

The development accelerators include thioether compounds described in Japanese Patent Publication for Opposition Purpose (hereinafter referred to as "J.P. KOKOKU") Nos. Sho 37-16088, 37-5987, 38-7826, 44-12380 and 45-9019, and U.S. Pat. No. 3,813,247; p-phenylenediamine compounds described in J.P. KOKAI Nos. 52-49829 and 50-155554; quaternary ammonium salts described in J.P. KOKAI No. Sho 50-137726, J.P. KOKOKU No. 44-30074, and J.P. KOKAI Nos. Sho 56-156826 and 52-43429; amine compounds described in U.S. Pat. Nos. 2,494,903, 3,128, 182, 4,230,796 and 3,253,919, J.P. KOKOKU No. Sho 41-11431, U.S. Pat. Nos. 2,482,546, 2,596,926 and 3,582, 346; polyalkylene oxides described in J.P. KOKOKU Nos. Sho 37-16088 and 42-25201, U.S. Pat. No. 3,128,183, J.P. KOKOKU Nos. Sho 41-11431 and 42-23883 and U.S. Pat. No. 3,532,501; as well as 1-phenyl-3-pyrazolidones and imidazoles. They can be used if necessary.

The amount of the color-developer replenisher is preferably not more than 550 ml, more preferably not more than 450 ml and most preferably in the range of 80 to 400 ml, per square meter of a photographic sensitive material. The amount of this replenisher can be reduced to less than 300 ml by reducing the bromide ion concentration in the replenisher or by using a bromide ion-free replenisher. For processing a photosensitive material for prints, the amount of this replenisher is 20 to 600 ml, preferably 30 to 200 ml, and more preferably 40 to 100 ml, per square meter of the photosensitive material.

For the photographic sensitive material, the processing temperature of the color developer is preferably not lower than 35° C., more preferably 40 to 50° C. For the photosensitive material for prints, the processing temperature of the color developer is 20 to 50° C., preferably 30 to 45° C. and more preferably 37 to 42° C.

The processing time with the color developer is preferably 30 seconds to three minutes and fifteen seconds, and more preferably thirty seconds to two minutes and thirty seconds for the photographic sensitive material, and is usually not longer than three minutes, preferably ten seconds to one minute, and more preferably ten to thirty seconds for the photosensitive material for prints. The processing time (such as development time) herein indicates a period of time necessitated after the photosensitive material is put into the processing solution and until it is put into a subsequent processing solution.

Preferably, the developer for the photographic material for prints is substantially free from benzyl alcohol. It is also preferred that the developer for the photographic material for prints is substantially free of sulfite ion so as to inhibit a change in the photographic properties due to the continuous process and also to obtain the effect of the present invention. The expression "substantially free of sulfite ion" herein indicates that the sulfite ion concentration is not higher than $3.0\times10^{-3}$ mol/l). More preferably, the sulfite ion concentration is not higher than $1.0\times10^{-3}$ mol/l, and most preferably, the developer is completely free of the sulfite ion except for a very small amount of the sulfite ion used for inhibiting the oxidation of a processing kit containing the concentrated developing agent to be used for preparing the developer. Further, it is preferred that the developer is substantially free of hydroxylamine (namely, the hydroxylamine concentration is not higher than $5.0\times10^{-3}$ mol/l) so as to inhibit the change of the photographic properties due to the change in the concentration of hydroxylamine. Most preferably, the developer is completely free of hydroxylamine.

It is preferred to inhibit the evaporation of the developer and oxidation thereof by air. The contact area of the processing liquid with air in the processing vessel can be represented by the opening rate defined as follows:

Opening rate=[(contact area of processing solution with air ($cm^2$))]/[volume of processing solution ($cm^3$)]

The opening rate ($cm^{-1}$) defined as above is preferably not higher than 0.05, more preferably in the range of 0.0005 to 0.01. The opening rate is reduced by covering the surface of the photographic processing solution in the processing vessel with a floating lid or the like, by providing a movable lid as described in J.P. KOKAI No. Hei 1-82033 or by a slit development process described in J.P. KOKAI No. Sho 63-216050. It is preferred that the processing solution in a color developer-replenishing tank or in a processing tank is shielded with a high-boiling organic solvent or a high-molecular compound to reduce the contact area thereof with air. It is particularly preferred to use liquid paraffin, an organosiloxane or the like. The opening rate can be reduced not only in the color development and black-and-white development steps but also in all of the subsequent steps such as bleaching, bleach-fixing, fixing, water washing and stabilization steps.

The developer can be reused after regeneration. The term "regeneration of the developer" herein indicates that the used developer is treated with an anion exchange resin or by electrodialysis and that the activity of the developer is increased by adding a processing agent called "regenerating agent". The regeneration rate (rate of the overflow in the replenisher) is preferably at least 70%, particularly at least 90%.

The 4-(N,N-dialkylamino)aniline compounds can be synthesized by a method shown below or a method similar to it. A method described on page 3,100 of Journal of the American Chemical Society, Vol. 73 (1951) can be referred to.

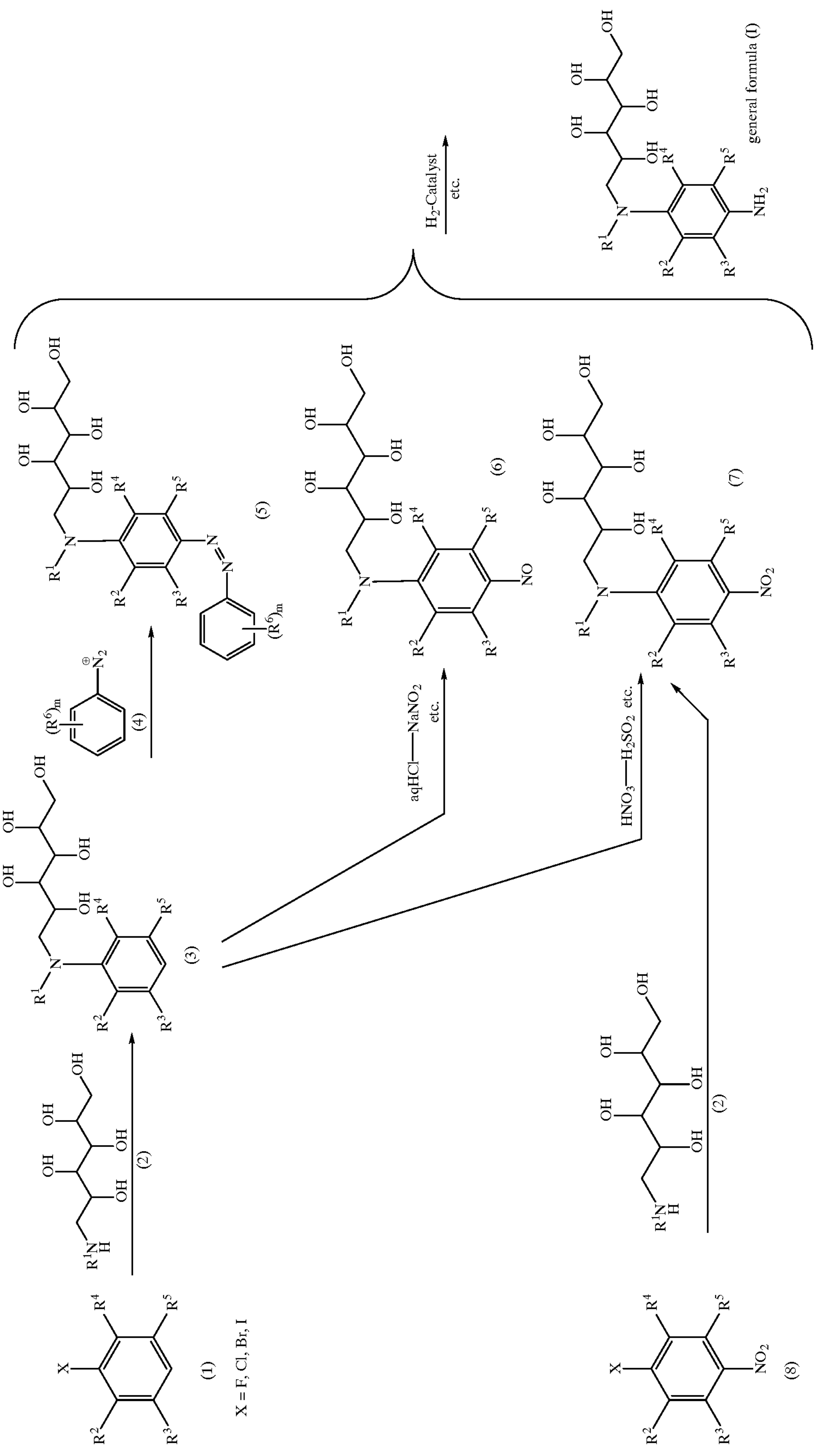
(2)
(4)
aqHCl—NaNO2 etc.
HNO3—H2SO2 etc.
H2-Catalyst etc.
(1)
X = F, Cl, Br, I
(3)
(5)
(6)
(7)
(8)
general formula (I)

According to the above reaction scheme, a compound (3) is obtained by the substitution reaction of a halobenzene compound (1) with an amino compound (2). Then, the azo coupling is conducted in the p-position to the amino group, or a nitroso group or nitro group is introduced thereinto, and the product is reduced (by catalytic reduction with hydrogen, reduction with zinc under acidic condition, reduction with reducing iron, or the like) to obtain the intended product.

The substitution reaction can be carried out also by replacing the above-described amino compound having $R^1$ with a corresponding $R^1$-free primary amine compound and introducing $R^1$ after the substitution reaction. The substitution reaction is carried out by using, for example, one equivalent of a fluorobenzene compound, chlorobenzene compound, bromobenzene compound or iodobenzene compound as the halobenzene compound (1) and one to five equivalents, preferably one to three equivalents, of the amino compound (2) in the absence of any base or in the presence of one to five equivalents, preferably one to three equivalents, of an organic base (such as triethylamine or diazabicycloundecene) or an inorganic base (such as sodium hydrogencarbonate, sodium carbonate, potassium carbonate, sodium hydroxide or potassium hydroxide); without using any solvent or in a solvent such as water, an amide solvent (such as N,N-dimethylacetamide, N,N-dimethylformamide or 1-methyl-2-pyrrolidone), a sulfone solvent (such as sulfolane), a sulfoxide solvent (such as dimethyl sulfoxide), an ureido solvent (such as tetramethylurea), an ether solvent (such as diethyl ether, tetrahydrofuran or dioxane) or an alcohol solvent (such as methanol, ethanol, isopropyl alcohol, butanol or ethylene glycol) alone or in combination of two or more of them; in the absence or presence of a catalyst [such as copper (I) iodide, tetra kistriphenylphosphine palladium (0) or palladium chloride alone or in combination of two or more of them]; at a reaction temperature in the range of 0 to 200° C., preferably 25 to 18° C.; for a reaction time in the range of 10 minutes to 72 hours, preferably 30 minutes to 12 hours.

Then the azo coupling at the p-position to the amino group is conducted, or a nitroso group or nitro group is introduced thereinto. An embodiment of the azo coupling is as follows: A substituted or unsubstituted aniline is converted into a diazonium salt thereof with an acid (organic or inorganic acid such as hydrochloric acid, sulfuric acid, methanesulfonic acid or acetic acid) without using any solvent or in water or an organic solvent (such as an alcohol solvent, e.g. methanol, ethanol or isopropyl alcohol, an amide solvent, e.g. N,N-dimethylacetamide, N,N-dimethylformamide or 1-methyl-2-pyrrolidone, a sulfone solvent, e.g. sulfolane, a sulfoxide solvent, e.g. dimethyl sulfoxide, or a ureido solvent, e.g. tetramethylurea) at a temperature in the range of −78 to 40° C., preferably −20 to 30° C. for a reaction time in the range of five minutes to five hours, preferably five minutes to one hour; and then one to five equivalents, preferably one to two equivalents, of the diazonium salt is coupled with an N,N-dialkylaniline without using any solvent or in water or an organic solvent (such as an alcohol solvent, e.g. methanol, ethanol or isopropyl alcohol, an amide solvent, e.g. N,N-dimethylacetamide, N,N-dimethylformamide or 1-methyl-2-pyrrolidone, a sulfone solvent, e.g. sulfolane, a sulfoxide solvent, e.g. dimethyl sulfoxide, or a ureido solvent, e.g. tetramethylurea) at a temperature in the range of −78 to 40° C. preferably −20 to 30° C. for a reaction time in the range of five minutes to five hours, preferably five minutes to one hour. The coupling reaction is preferably conducted under a weakly acidic to weakly basic condition. The nitrosation is conducted by, for example, using one to five equivalents, preferably one to two equivalents, of a nitrosating agent without using any solvent or in water or an organic solvent (such as an alcohol solvent, e.g. methanol, ethanol or isopropyl alcohol, an amide solvent, e.g. N,N-dimethylacetamide, N,N-dimethylformamide or 1-methyl-2-pyrrolidone, a sulfone solvent, e.g. sulfolane, a sulfoxide solvent, e.g. dimethyl sulfoxide, or a ureido solvent, e.g. tetramethylurea) at a temperature in the range of −78 to 40° C. preferably −20 to 30° C. for a reaction time in the range of five minutes to five hours, preferably five minutes to one hour. The nitration is conducted by, for example, using one to five equivalents, preferably one to two equivalents, of a nitrating agent of a concentration in the range of 60 to 98% alone or in combination with an activator such as sulfuric acid, sulfuric anhydride, acetic anhydride or trifluoroacetic acid without using any solvent or in water or an organic solvent (such as an alcohol solvent, e.g. methanol, ethanol or isopropyl alcohol, an organic acid, e.g. acetic acid, an organic acid anhydride, e.g. acetic anhydride or trifluoroacetic anhydride, an amide solvent, e.g. N,N-dimethylacetamide, N,N-dimethylformamide or 1-methyl-2-pyrrolidone, a sulfone solvent, e.g. sulfolane, a sulfoxide solvent, e.g. dimethyl sulfoxide, or a ureido solvent, e.g. tetramethylurea) at a temperature in the range of −78 to 100° C., preferably −20 to 30° C., for a reaction time in the range of five minutes to five hours, preferably five minutes to one hour.

It is also preferred to use a halobenzene (8) having a nitro group in the 4-position to directly obtain a corresponding 4-aminonitrobenzene (7).

Finally, the product is reduced by the catalytic reduction with hydrogen, reduction with zinc under an acidic condition or reduction with reduced iron to obtain the intended product. The catalytic reduction with hydrogen is conducted, for example, in the presence of a catalyst (such as palladium-carbon or Raney nickel) without using any solvent or in water or an organic solvent (such as an alcohol, e.g. methanol, ethanol or isopropyl alcohol, an amide, e.g. N,N-dimethylacetamide, N,N-dimethylformamide or 1-methyl-2-pyrrolidone, a sulfone, e.g. sulfolane, a sulfoxide, e.g. dimethyl sulfoxide, or a ureido, e.g. tetramethylurea) at a reaction temperature in the range of 0 to 150° C., preferably 0 to 50° C., under a hydrogen pressure in the range of 1 to 500 atm, preferably 1 to 200 atm. for a reaction time in the range of 5 minutes to 72 hours, preferably 1 to 8 hours. The reduction with reduced iron is conducted, for example, with 4 to 10 equivalents, preferably 4 to 6 equivalents, of reduced iron and 0.0001 to 1 equivalent, preferably 0.001 to 0.1 equivalent, of an acid (an inorganic acid such as hydrochloric acid or sulfuric acid or an organic acid such as acetic acid or methanesulfonic acid) or an acid salt (such as ammonium chloride, sodium chloride or sodium sulfate) alone or in combination of two or more of them without using any solvent or in water or an organic solvent (such as an alcohol, e.g. methanol, ethanol or isopropyl alcohol, an amide, e.g. N,N-dimethylacetamide, N,N-dimethylformamide or 1-methyl-2-pyrrolidone, a sulfone, e.g. sulfolane, a sulfoxide, e.g. dimethyl sulfoxide, or a ureido, e.g. tetramethylurea) at a reaction temperature in the range of 0 to 150° C., preferably 50 to 100° C., for a reaction time in the range of 30 minutes to 72 hours, preferably 1 to 8 hours. The reduction with zinc under an acidic condition is conducted by using 3 to 10 equivalents, preferably 3 to 6 equivalents, of zinc powder in the presence of an acid (an organic acid such as acetic acid or methanesulfonic acid, or an inorganic acid such as hydrochloric acid or sulfuric acid) without using any solvent or in water or an organic solvent (such as an alcohol, e.g. methanol, ethanol or isopropyl alcohol, an organic acid, e.g. acetic acid, an amide, e.g. N,N-dimethylacetamide, N,N-dimethylformamide or 1-methyl-2-pyrrolidone, a sulfone, e.g. sulfolane, a sulfoxide, e.g. dimethyl sulfoxide, a ureido, e.g. tetramethylurea, or an organic acid such as acetic acid, propionic acid or methanesulfonic acid) at a reaction temperature in the range of 0 to 150° C., preferably 0 to 100° C., for a reaction time in the range of 5 minutes to 72 hours, preferably 30 minutes to 3 hours.

the saccharide group in the course of the introduction or finally.

The alkylation is conducted, for example, by using 1 to 5 equivalents, preferably 1 to 3 equivalents, per equivalent of the alkyl group to be introduced, of a corresponding alkyl halide (such as chloride, bromide or iodide), an alkyl sulfonate (such as mesylate or tosylate) or an alkyl ester (such as acetate or benzoate) as the alkylating agent and 1 to 5 equivalents, preferably 1 to 3 equivalents, per equivalent of the alkyl group to be introduced, of an organic base (such as triethylamine or diazabicycloundecene) or an inorganic base (such as sodium hydrogencarbonate, sodium carbonate, potassium carbonate, sodium hydroxide or potassium hydroxide) without using any solvent or in a solvent such as water, an amide (e.g. N,N-dimethylacetamide, N,N-dimethylformamide or 1-methyl-2-pyrrolidone), a sulfone (e.g. sulfolane), a sulfoxide (e.g. dimethyl sulfoxide), a ureido (e.g. tetramethylurea), an ether (e.g. dioxane) or an alcohol (e.g. isopropyl alcohol or butanol) in the absence or presence of a catalyst (such as sodium iodide) at a reaction temperature in the range of 0 to 200° C., preferably 30 to 170° C.,

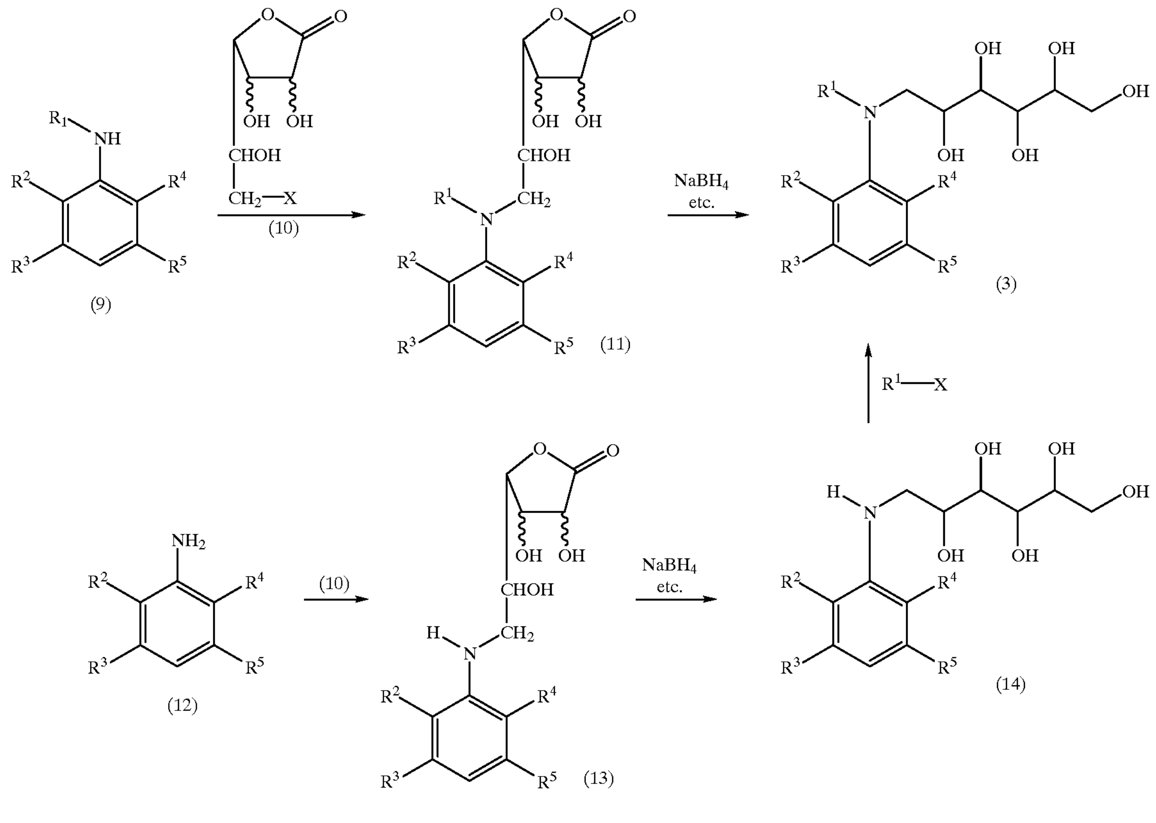

X = Cl, Br, I etc.

The compound (3) can be obtained by, for example, the alkylation of an aniline compound as described above. In particular, a saccharide group derivative (10) is introduced into a secondary aniline (9); or the saccharide group derivative (10) is introduced into a primary aniline (12), then $R^1$ is introduced thereinto and, if necessary, it is converted into for a reaction time in the range of 10 minutes to 72 hours, preferably 30 minutes to 12 hours.

The products obtained by the above-described reactions are after-treated as in ordinary organic synthesis reactions and then purified if necessary. Namely, for example, the product isolated from the reaction system can be used without the purification or after the purification by the recrystallization, column chromatography or the like, or a combination of these techniques. It is also possible to use the product, after the completion of the reaction, by distilling off the reaction solvent or if necessary, pouring the product into water or ice, neutralizing it if necessary, and purifying the isolated product by the recrystallization, column chromatography or the like or by a combination of these techniques, if necessary. Alternatively, it is also possible to use the product, after the completion of the reaction, by distilling off the reaction solvent if necessary, pouring the product into water or ice, neutralizing it if necessary, extracting the product with an organic solvent and purifying the extract, if necessary, by the crystallization or column chromatography or by the combination of these techniques.

The following Examples will further illustrate the present invention, which by no means limit the invention.

EXAMPLE 1

The compound (D-1-a) of the present invention was synthesized according to the following reaction scheme:

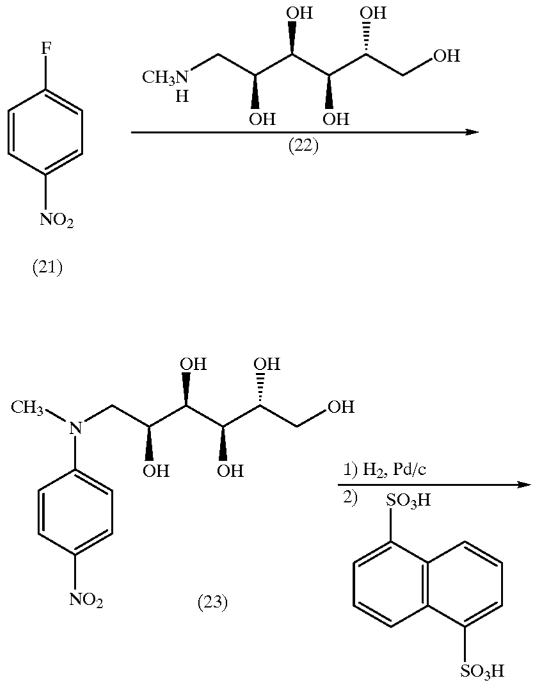

(21) (22) (23)

-continued

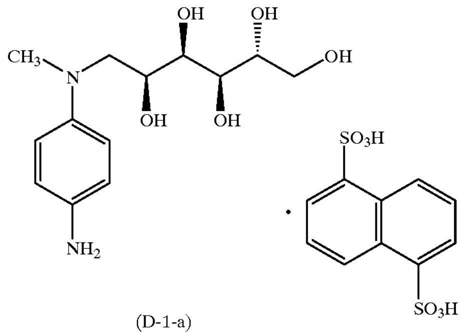

(D-1-a)

Synthesis of Compound (23):

42.3 g of the compound (21), 70.3 g of N-methyl-D-glucamine [compound (22)], 200 ml of acetonitrile and 50 ml of water were fed into a three-necked flask. 50.2 ml of triethylamine was dropped into the resultant mixture under stirring, heating and reflux for a period of 10 minutes. After the completion of the dropping, the obtained mixture was stirred as it was under heating and reflux for 8 hours, and then cooled to 70° C. After the extraction with 100 ml of water, 150 ml of ethyl acetate and 200 ml of hexane, the obtained aqueous layer was washed with a mixed solvent comprising 150 ml of ethyl acetate and 150 ml of hexane three times. In the course of the extraction and washing, the internal temperature was kept at 50° C. or higher. 300 ml of water was added to the aqueous solution thus obtained. After stirring under cooling with water, crystals thus formed were filtered by means of suction and dried to obtain 73.1 g of the intended compound (23) (yield: 77%).

Synthesis of Compound (D-1-a):

73.1 g of the compound (23), 7 g of palladium/carbon (10%) and 220 ml of methanol were fed into an autoclave and stirred at room temperature under a hydrogen pressure of 100 atm. for 8 hours. A solution of 83.2 g of naphthalene-1,5-disulfonic acid tetrahydrate in 200 ml of methanol was added to the reaction mixture. The obtained mixture was filtered, and the filtrate was concentrated with a rotary evaporator. The solvent was distilled off under reduced pressure with a vacuum pump to obtain 127 g of the intended compound (D-1-a) (yield: 96%).

EXAMPLE 2

The compound (D-2-a) of the present invention was synthesized according to the following reaction scheme:

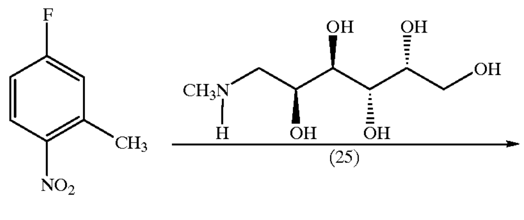

(24) (25)

-continued

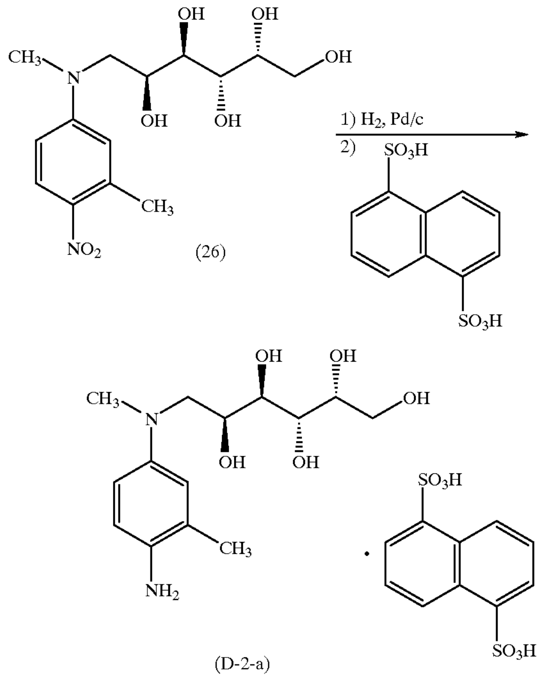

(26)

(D-2-a)

Synthesis of Compound (26):

39.4 g of the compound (24), 59.6 g of 1-deoxy-1-(methylamino)-D-galactitol [compound (25)], 140 ml of acetonitrile and 40 ml of water were fed into a three-necked flask. 42.5 ml of triethylamine was dropped into the resultant mixture under stirring, heating and reflux for a period of 10 minutes. After the completion of the dropping, the obtained mixture was stirred as it was under heating and reflux for 8 hours, and then cooled to 70° C. After the extraction with 50 ml of water, 100 ml of ethyl acetate and 100 ml of hexane, the obtained aqueous layer was washed with a mixed solvent comprising 150 ml of ethyl acetate and 150 ml of hexane three times. In the course of the extraction and washing, the internal temperature was kept at 50° C. or higher. 300 ml of water was added to the aqueous solution thus obtained. After stirring under cooling with water, crystals thus formed were filtered by means of suction and dried to obtain 58.7 g of the intended compound (26) (yield: 70%).

Synthesis of Compound (D-2-a):

58.7 g of the compound (26), 5 g of palladium/carbon (10%) and 150 ml of methanol were fed into an autoclave and stirred at room temperature under a hydrogen pressure of 100 atm. for 8 hours. A solution of 63.9 g of naphthalene-1,5-disulfonic acid tetrahydrate in 100 ml of methanol was added to the reaction mixture. The obtained mixture was filtered, and the filtrate was concentrated with a rotary evaporator. The solvent was distilled off under reduced pressure with a vacuum pump to obtain 105 g of the intended compound (D-2-a) (yield: 100%).

EXAMPLE 3

The compound (D-88-a) of the present invention was synthesized according to the following reaction scheme:

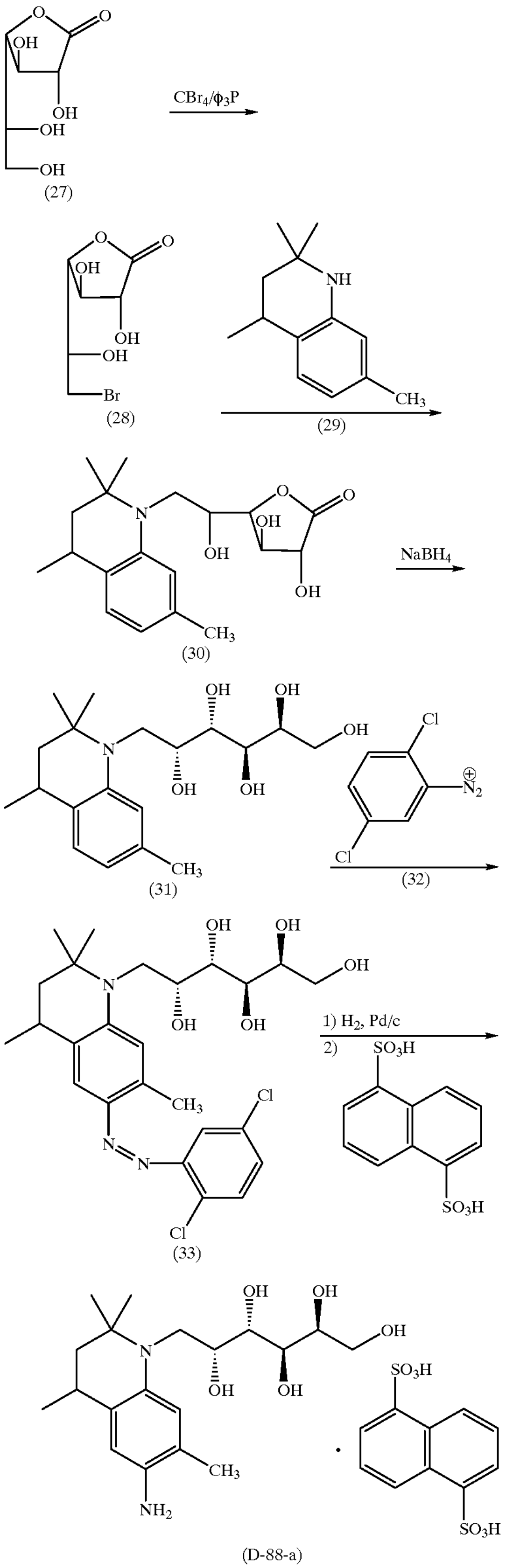

(27)

(28)

(29)

(30)

(31)

(32)

(33)

(D-88-a)

Synthesis of Compound (28):

25.0 g of 7 -D-galactonolactone [compound (27)] and 500 ml of pyridine were fed into a three-necked flask. 73.5 g of triphenylphosphine was added to the resultant mixture under stirring at room temperature and then 46.9 g of carbon tetrabromide was dropped thereinto for a period of 30 minutes. After the completion of the dropping, the obtained mixture was stirred as it was at room temperature for 2 hours. 140 ml of methanol was dropped into the mixture for a period of 10 minutes. The solvent was distilled off with an aspirator while the internal temperature was kept at 60° C. or below under reduced pressure. 100 ml of water and 250 ml of toluene were added to the residue to conduct the extraction. The obtained aqueous layer was distilled off with the aspirator at an internal temperature of 60° C. or below under reduced pressure to distill off 50 ml of low-boiling components mainly comprising water. After the extraction with 100 ml of ethyl acetate eight times, the obtained ethyl acetate layer was dried with anhydrous sodium sulfate and left to stand overnight to form crystals, which were filtered to obtain 28.0 g of the intended compound (28) (yield: 83%).

Synthesis of Compound (30):

47.3 g of the compound (29), 22.5 g of sodium iodide, 63 g of sodium hydrogencarbonate and 140 ml of N,N-dimethylacetamide were fed into a three-necked flask. 72.3 g of the compound (28) was dropped into the resultant mixture for a period of 15 minutes under stirring and heating to keep the internal temperature at 90° C. After the completion of the dropping, the resultant mixture was stirred under heating to keep the internal temperature at 90 to 95° C. for 28 hours, and then cooled to 30° C. One liter of ethyl acetate and 700 ml of water were added to the reaction mixture and the mixture was stirred to conduct the extraction. The ethyl acetate layer thus obtained was washed with a mixed solution of 600 ml of water and 200 ml of saturated aqueous common salt solution four times, and then dried over anhydrous sodium sulfate. The product was concentrated with a rotary evaporator. The obtained residue was purified by silica gel column chromatography to obtain 65.0 g of the intended compound (30) (yield: 75%).

Synthesis of Compound (31):

26.0 g of the compound (30) and 150 ml of methanol were fed into a three-necked flask. Then 5.7 g of sodium boron hydride was slowly added to the resultant mixture for a period of five minutes. After the completion of the addition followed by stirring under heating and reflux for two hours, the reaction mixture was cooled to 30° C. and concentrated with an aspirator under reduced pressure. An aqueous solution of 10 g of sodium hydroxide in 20 ml of water was added to the concentrate, and the resultant mixture was concentrated with the aspirator under reduced pressure. The residue thus obtained was purified according to the silica gel column chromatography to obtain 20.0 g of the intended compound (31) (yield: 76%).

Synthesis of Compound (33):

15.7 g of 2,5-dichloroaniline and 90 ml of water were fed into a three-necked flask. 31 ml of sulfuric acid was added to the resultant mixture under stirring and under cooling with ice. A solution of 7.4 g of sodium nitrite in 20 ml of water was dropped into the mixture for a period of ten minutes while the internal temperature was kept at 8° C. or below. After the completion of the dropping, the stirring was continued for thirty minutes. 20.0 g of the compound (31), 55.4 g of sodium acetate, 38 ml of acetic acid and 75 ml of methanol were fed into another three-necked flask, and the diazonium salt solution prepared as described above was added thereto under stirring and under cooling with ice while the internal temperature was kept at 16° C. or lower. In the course of the reaction, the reaction was traced by TLC, and the addition of the diazonium salt solution was completed when the compound (31) disappeared in the reaction system. After the completion of the addition followed by the stirring for thirty minutes, methanol was distilled off under reduced pressure. The reaction mixture was poured into ice and neutralized with a sodium hydroxide solution. After the extraction with one liter of ethyl acetate and 700 ml of water, the obtained ethyl acetate layer was washed with a mixed solution of 700 ml of water and 100 ml of saturated aqueous common salt solution four times and then dried over anhydrous sodium sulfate. The product was concentrated with a rotary evaporator, and the obtained residue was purified by silica gel column chromatography to obtain 20.0 g of the intended compound (33) (yield: 67%).

Synthesis of Compound (D-88-a):

20.0 g of the compound (33), 1 g of palladium/carbon (10%) and 80 ml of methanol were fed into an autoclave, and stirred at room temperature under a hydrogen pressure of 100 atm. for eight hours. A solution of 13.7 g of naphthalene-1,5-disulfonic acid in 25 ml of methanol was added to the reaction mixture. After the filtration, the filtrate was concentrated with a rotary evaporator. 150 ml of ethyl acetate and 150 ml of water were added to the concentrate, and the resultant mixture was stirred to obtain a solution. After the separation into layers, the aqueous layer was further washed with 150 ml of ethyl acetate three times. The aqueous layer thus obtained was concentrated with a rotary evaporator and then 50 ml of methanol was added thereto to obtain a solution. Crystals thus formed were filtered by means of suction to obtain 22.0 g of the intended compound (D-88-a) (yield: 88%).

EXAMPLE 4

A multilayer color photosensitive material, which will be referred to as "sample 101", was prepared by forming layers of the following compositions on a subbed cellulose triacetate film support: (Compositions of photosensitive layers)

Main materials to be used for forming the layers are classified as follows:

ExC: cyan coupler
ExM: magenta coupler
ExY: yellow coupler
ExS: sensitizing dye
UV: ultraviolet absorber
HBS: high-boiling organic solvent
H: gelatin hardener The numerals for the respective components indicate the respective amounts of coatings given by g/$m^2$. Those for silver halides are given in terms of silver. Those for sensitizing dyes are given in terms of molar unit per mol of the silver halide contained in the same layer.

(Sample 101)

The first layer (antihalation layer):

| | | |
|---|---|---|
| black colloidal silver | silver | 0.18 |
| gelatin | | 1.40 |
| ExM-1 | | 0.18 |
| ExF-1 | | $2.0 \times 10^{-3}$ |

The second layer (intermediate layer):

| | | |
|---|---|---|
| emulsion G | silver | 0.065 |
| 2,5-di-t-pentadecylhydroquinone | | 0.18 |
| ExC-2 | | 0.020 |
| UV-1 | | 0.060 |
| UV-2 | | 0.080 |
| UV-3 | | 0.10 |
| HBS-1 | | 0.10 |
| HBS-2 | | 0.020 |
| gelatin | | 1.04 |

The third layer (low-speed red-sensitive emulsion layer)

| | | |
|---|---|---|
| emulsion A | silver | 0.25 |
| emulsion B | silver | 0.25 |
| ExS-1 | | $6.9 \times 10^{-4}$ |
| ExS-2 | | $1.8 \times 10^{-5}$ |
| ExS-3 | | $3.1 \times 10^{-4}$ |
| ExC-1 | | 0.17 |
| ExC-4 | | 0.17 |
| ExC-7 | | 0.020 |
| UV-1 | | 0.070 |
| UV-2 | | 0.050 |
| UV-3 | | 0.070 |
| HBS-1 | | 0.060 |
| gelatin | | 1.0 |

The fourth layer (medium-speed red-sensitive emulsion layer)

| | | |
|---|---|---|
| emulsion D | silver | 0.80 |
| ExS-1 | | $3.5 \times 10^{-4}$ |
| ExS-2 | | $1.6 \times 10^{-5}$ |
| ExS-3 | | $5.1 \times 10^{-4}$ |
| ExC-1 | | 0.20 |
| ExC-2 | | 0.050 |
| ExC-4 | | 0.20 |
| ExC-5 | | 0.050 |
| ExC-7 | | 0.015 |
| UV-1 | | 0.070 |
| UV-2 | | 0.050 |
| UV-3 | | 0.070 |
| gelatin | | 1.50 |

The fifth layer (high-speed red-sensitive emulsion layer)

| | | |
|---|---|---|
| emulsion E | silver | 1.40 |
| ExS-1 | | $2.4 \times 10^{-4}$ |
| ExS-2 | | $1.0 \times 10^{-4}$ |
| ExS-3 | | $3.4 \times 10^{-4}$ |
| ExC-1 | | 0.097 |
| ExC-2 | | 0.010 |
| ExC-3 | | 0.065 |
| ExC-6 | | 0.020 |

-continued

| | |
|---|---|
| HBS-1 | 0.22 |
| HBS-2 | 0.10 |
| gelatin | 1.63 |

The sixth layer (intermediate layer)

| | |
|---|---|
| Cpd-1 | 0.040 |
| HBS-1 | 0.020 |
| gelatin | 0.80 |

The seventh layer (low-speed green-sensitive emulsion layer)

| | | |
|---|---|---|
| emulsion C | silver | 0.30 |
| ExS-4 | | $2.6 \times 10^{-5}$ |
| ExS-5 | | $1.8 \times 10^{-4}$ |
| ExS-6 | | $6.9 \times 10^{-4}$ |
| ExM-1 | | 0.021 |
| ExM-2 | | 0.26 |
| ExM-3 | | 0.030 |
| ExY-1 | | 0.025 |
| HBS-1 | | 0.10 |
| HBS-3 | | 0.010 |
| gelatin | | 0.75 |

The eighth layer (medium-speed green-sensitive emulsion layer)

| | | |
|---|---|---|
| emulsion D | silver | 0.55 |
| ExS-4 | | $2.2 \times 10^{-5}$ |
| ExS-5 | | $1.5 \times 10^{-4}$ |
| ExS-6 | | $5.8 \times 10^{-4}$ |
| ExM-2 | | 0.094 |
| ExM-3 | | 0.026 |
| ExY-1 | | 0.018 |
| HBS-1 | | 0.16 |
| HBS-3 | | $8.0 \times 10^{-3}$ |
| gelatin | | 0.55 |

The ninth layer (high-speed green-sensitive emulsion layer)

| | | |
|---|---|---|
| emulsion E | silver | 1.55 |
| ExS-4 | | $4.6 \times 10^{-5}$ |
| ExS-5 | | $1.0 \times 10^{-4}$ |
| ExS-6 | | $3.9 \times 10^{-4}$ |
| ExC-1 | | 0.015 |
| ExM-1 | | 0.013 |
| ExM-4 | | 0.065 |
| ExM-5 | | 0.019 |
| HBS-1 | | 0.25 |
| HBS-2 | | 0.10 |
| gelatin | | 1.54 |

The tenth layer (yellow filter layer)

| | | |
|---|---|---|
| yellow colloidal silver | silver | 0.035 |
| Cpd-1 | | 0.080 |
| HBS-1 | | 0.030 |
| gelatin | | 0.95 |

The eleventh layer (low-speed blue-sensitive emulsion layer)

| | | |
|---|---|---|
| emulsion C | silver | 0.18 |
| ExS-7 | | $8.6 \times 10^{-4}$ |
| ExY-1 | | 0.042 |
| ExY-2 | | 0.72 |
| HBS-1 | | 0.28 |
| gelatin | | 1.30 |

The twelfth layer (medium-speed blue-sensitive emulsion layer)

| emulsion D | silver 0.40 |
|---|---|
| ExS-7 | $7.4 \times 10^{-4}$ |
| ExC-7 | $7.0 \times 10^{-3}$ |
| ExY-2 | 0.15 |
| HBS-1 | 0.050 |
| gelatin | 0.85 |

The thirteenth layer (high-speed blue-sensitive emulsion layer)

| emulsion F | silver 0.70 |
|---|---|
| ExS-7 | $2.8 \times 10^{-4}$ |
| ExY-2 | 0.20 |
| HBS-1 | 0.070 |
| gelatin | 0.69 |

The fourteenth layer (the first protective layer)

| emulsion G | silver 0.20 |
|---|---|
| UV-4 | 0.11 |
| UV-5 | 0.17 |
| HBS-1 | $5.0 \times 10^{-2}$ |
| gelatin | 1.00 |

The fifteenth layer (the second protective layer)

| | |
|---|---|
| H-1 | 0.40 |
| B-1 (diameter: 1.7 μm) | $5.0 \times 10^{-2}$ |
| B-2 (diameter: 1.7 μm) | 0.10 |
| B-3 | 0.10 |
| S-1 | 0.20 |
| gelatin | 1.20 |

Further, the respective layers suitably contain W-1 to W-3, B-4 to B-6, F-1 to F-17, iron salts, lead salts, gold salts, platinum salts, iridium salts and rhodium salts in order to improve the storability, processability, pressure resistance, mildew-proofing and bacteria-proofing properties, antistatic properties and coating easiness.

TABLE 1

| Emulsion | Average AgI content (%) | Average grain diameter (μm) (μm) | Coefficient of variation of grain diameter (%) | Diameter/thickness ratio |
|---|---|---|---|---|
| A | 4.0 | 0.45 | 27 | 1 |
| B | 8.9 | 0.70 | 14 | 1 |
| C | 2.0 | 0.55 | 25 | 7 |
| D | 9.0 | 0.65 | 25 | 6 |
| E | 9.0 | 0.85 | 23 | 5 |
| F | 14.5 | 1.25 | 25 | 3 |
| G | 1.0 | 0.07 | 15 | 1 |

| Emulsion | Silver amount ratio (core/intermediate/shell) (AgI content) | Grain structure/shape |
|---|---|---|
| A | (1/3) (13/1) | double structure, octahedral grain |
| B | (3/7) (25/1) | double structure, octahedral grain |
| C | — | homogeneous structure, tabular grains |
| D | (12/59/29) (0/11/8) | triple structure, tabular grains |
| E | (8/59/33) (0/11/8) | triple structure, tabular grains |
| F | (37/63) (34/3) | double structure, tabular grains |
| G | — | homogeneous structure, fine grains |

In Table 1:

(1) The emulsions A to F were reduction-sensitized with thiourea dioxide and thiosulfonic acid in the step of preparation of the grains as described in an Example of J.P. KOKAI No. Hei 2-191938.

(2) The emulsions A to F were sensitized by gold sensitization, sulfur sensitization and selenium sensitization methods in the presence of a spectral sensitizing dye mentioned above for each photosensitive layer and sodium thiocyanate as described in an Example of J.P. KOKAI No. Hei 3-237450.

(3) In the preparation of tabular grains, a low-molecular weight gelatin was used as described in an Example of J.P. KOKAI No. Hei 1-158426.

(4) Dislocation lines as described in J.P. KOKAI No. Hei 3-237450 are observed on the tabular grains and normal crystal grains having a grain structure with a high-voltage electron microscope.

ExC-1
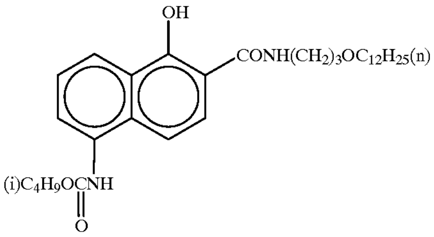
ExC-2
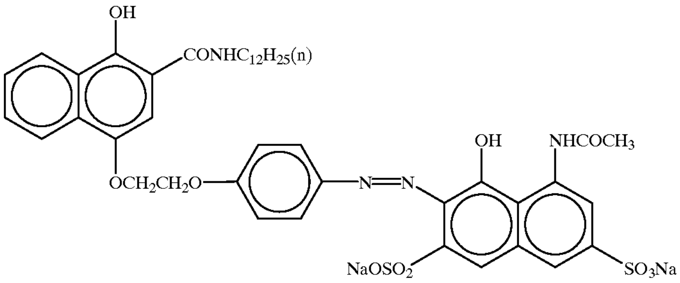
ExC-3
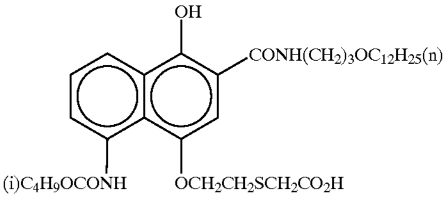
ExC-4
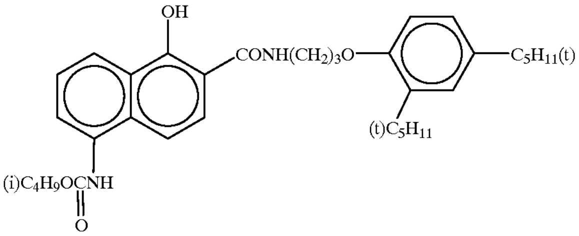
ExC-5
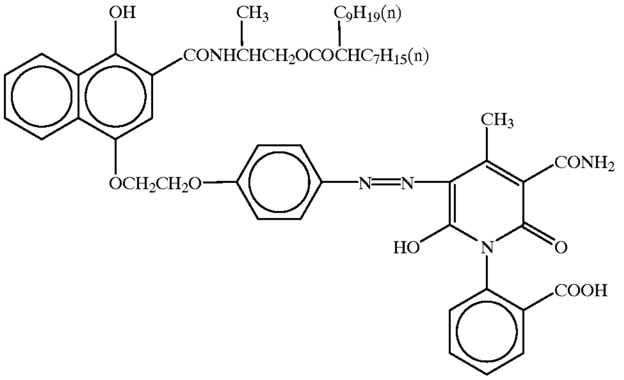

-continued
ExC-6
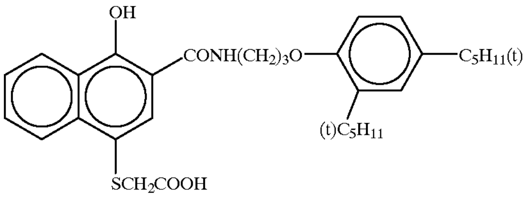
ExC-7
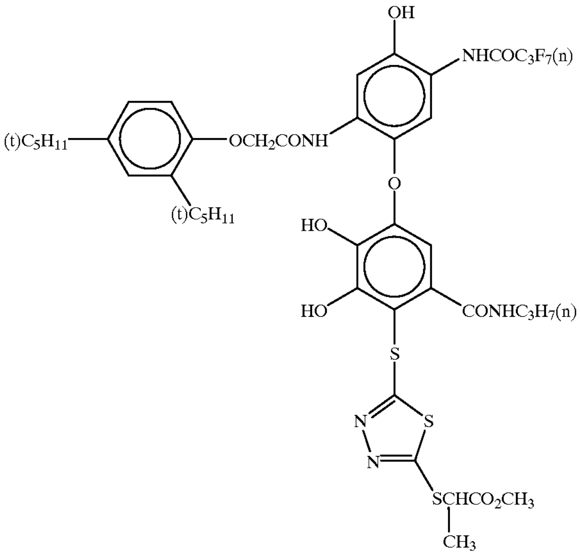
ExM-1
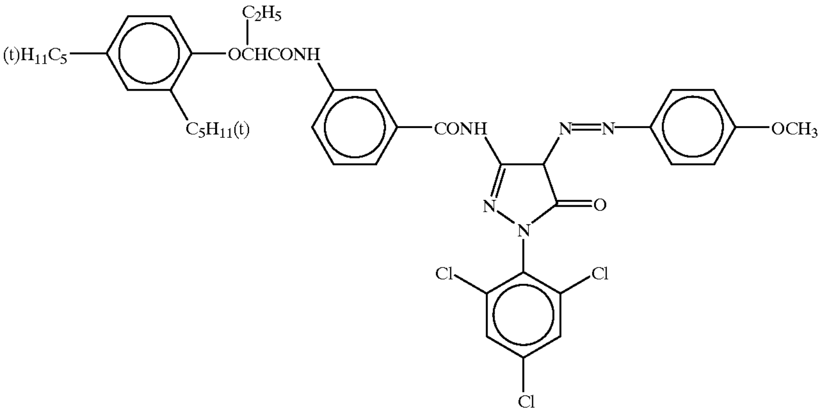
ExM-2
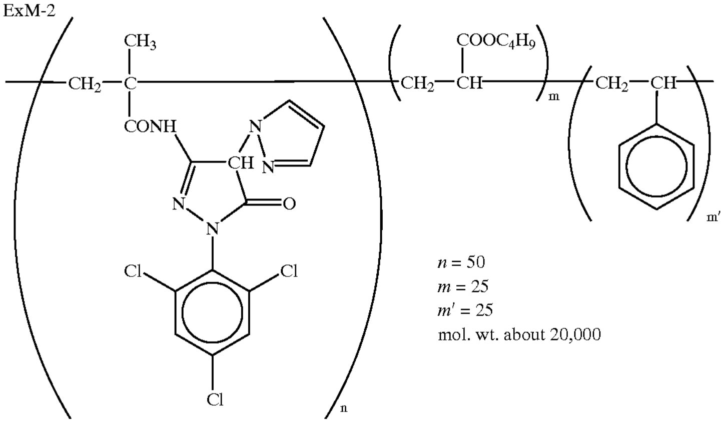
$n = 50$
$m = 25$
$m' = 25$
mol. wt. about 20,000

-continued
ExM-3
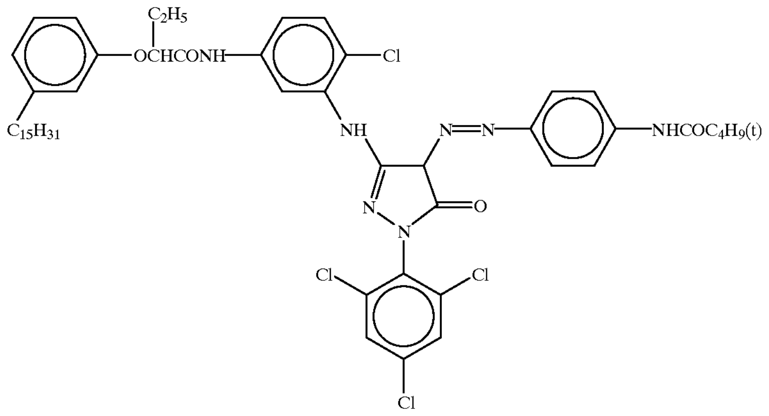
ExM-4
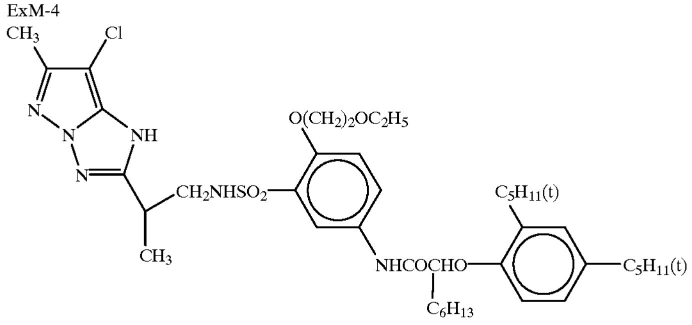
ExM-5
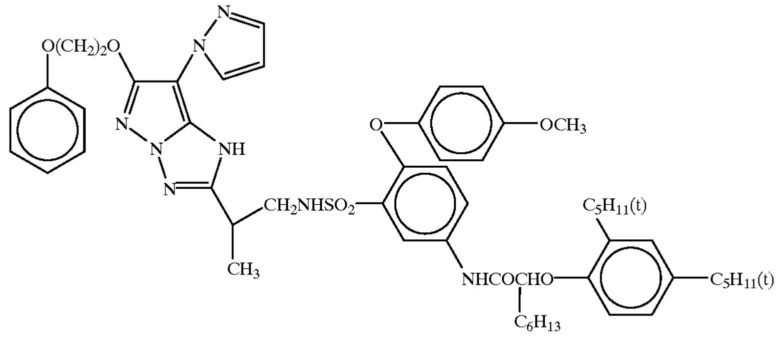
ExY-1
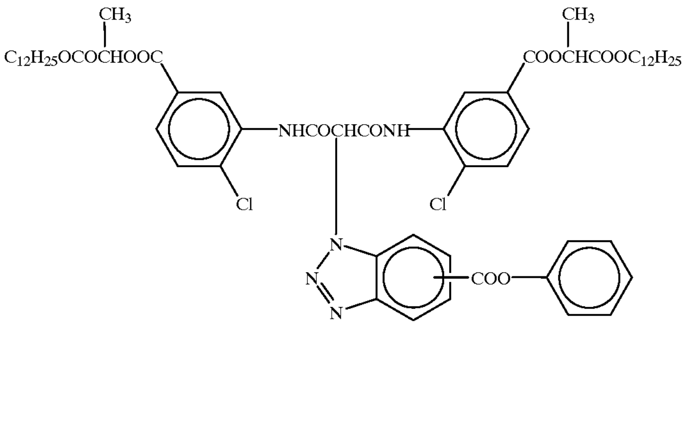

-continued
ExY-2
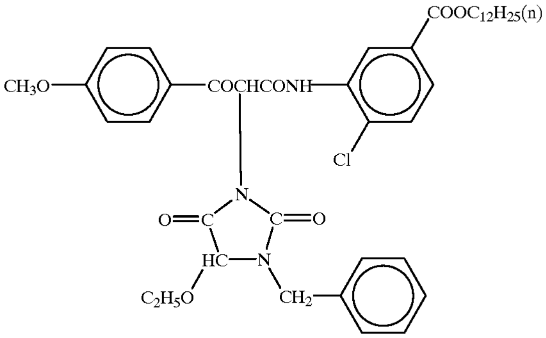
ExF-1
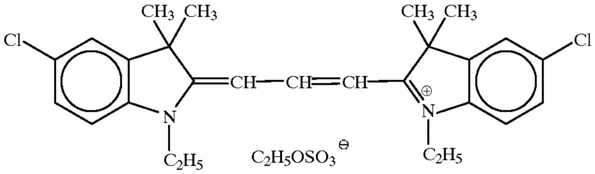
Cpd-1
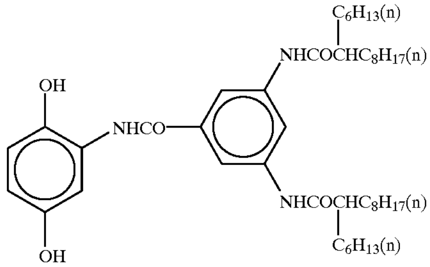
UV-1
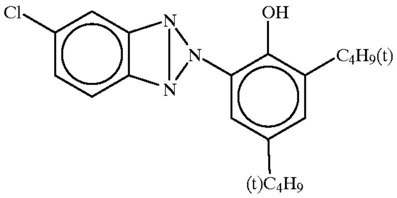
UV-2
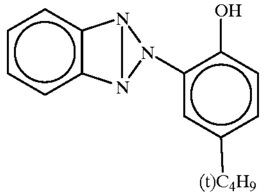
UV-3
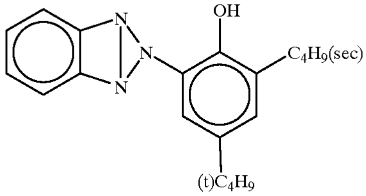
UV-4
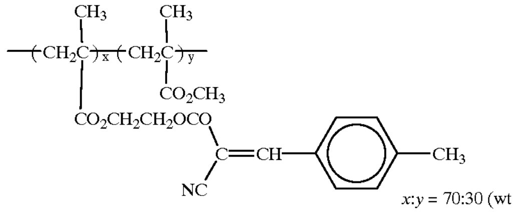
$x$:$y$ = 70:30 (wt %)
UV-5
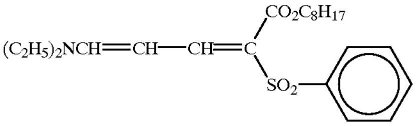
HBS-1
Tricresyl phosphate
HBS-2
Di-n-butyl phthalate
HBS-3
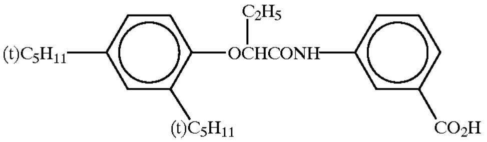
ExS-1
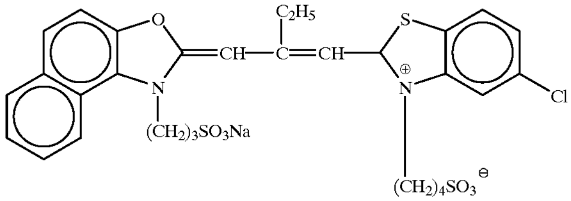
ExS-2
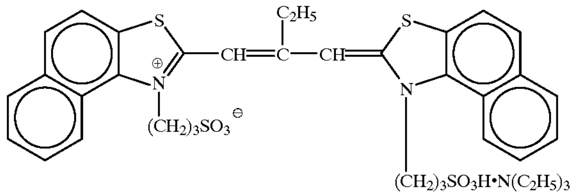

-continued
ExS-3
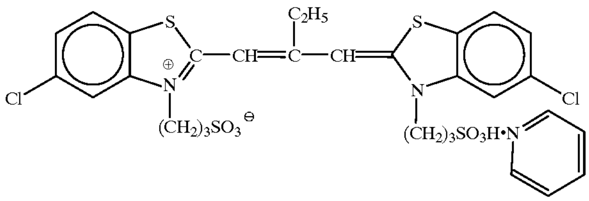
ExS-4
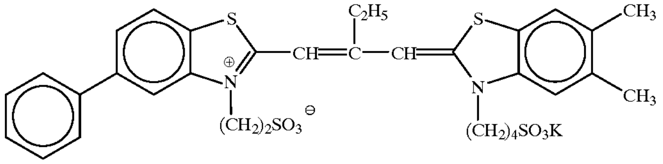
ExS-5
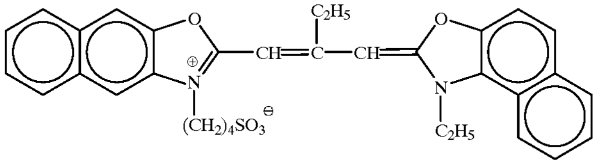
ExS-6
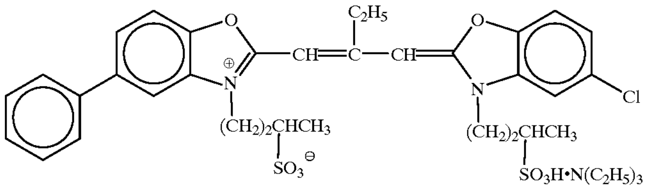
ExS-7
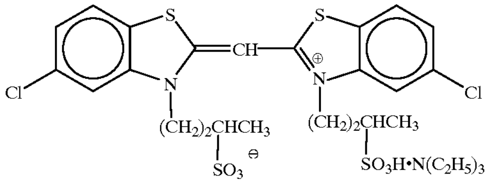
S-1
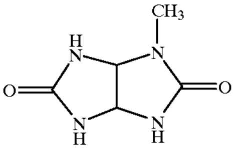
H-1
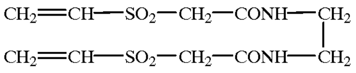
B-1
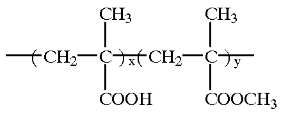
$x/y = 10/90$
B-2
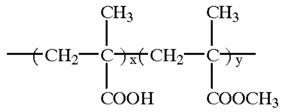
$x/y = 40/60$
B-3
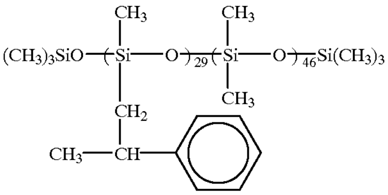
B-4
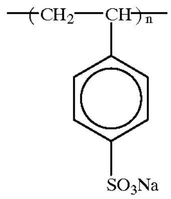
average molecular weight 750,000
B-5
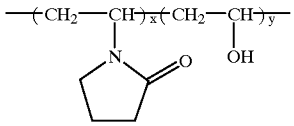
$x/y = 70/30$ -continued
B-6
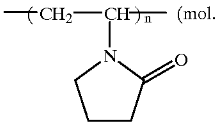
(mol. wt. about 10,000)
W-1
$C_8F_{17}SO_2NHCH_2CH_2CH_2OCH_2CH_2\overset{\oplus}{N}(CH_3)_3$
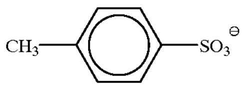
W-2
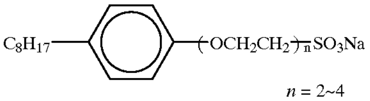
$n = 2\sim4$
W-3
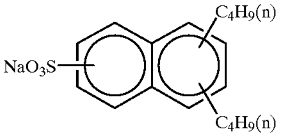
F-1
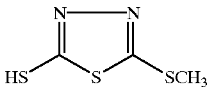
F-2
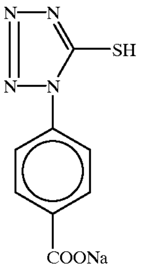
F-3
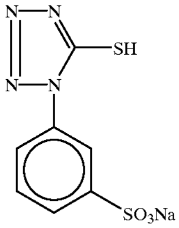
F-4
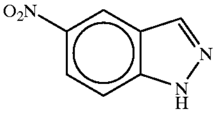
F-5
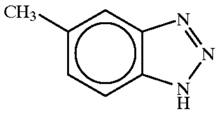
F-6
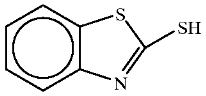
F-7
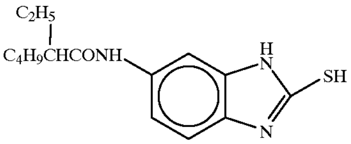
F-8
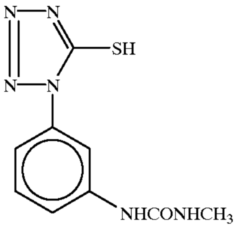
F-9
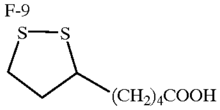
F-10
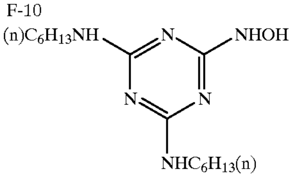
F-11
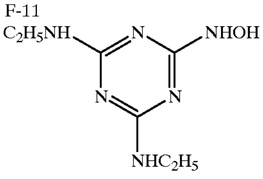
F-12
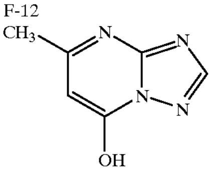

-continued

F-13

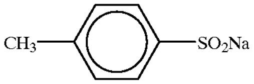

F-14

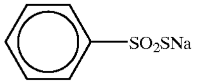

F-15

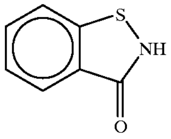

F-16

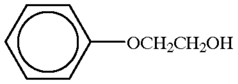

F-17

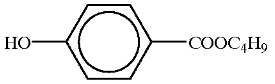

After exposing the above-described color photographic photosensitive material, it was processed by the following method with an automatic developing machine until the total quantity of the developer replenisher had become three times as much as the capacity of the tank.

(Processing method)

| (Step) | (Process) time) | (Process temp.) | (Amount of replenisher) | (Tank capacity) |
|---|---|---|---|---|
| Color development | 3 min 15 sec | 38° C. | 22 ml | 20 l |
| Bleaching | 3 min 00 sec | 38° C. | 25 ml | 40 l |
| Washing with water | 30 sec | 24° C. | 1200 ml | 20 l |
| Fixing | 3 min 00 sec | 38° C. | 25 ml | 30 l |
| Washing with water (1) | 30 sec | 24° C. | countercurrent pipe system from (2) to (1) | 10 l |
| Washing with water (2) | 30 sec | 24° C. | 1200 ml | 10 l |
| Stabilization | 30 sec | 38° C. | 25 ml | 10 l |
| Drying | 4 min 20 sec | 55° C. | | |

* The quantity of the replenisher was given per 35 mm width x 1 m length.

The composition of each of the processing liquids was as follows:

| | Mother liquor (g) | Replenisher (g) |
|---|---|---|
| (Color developer) | | |
| Diethylenetriaminepentaacetic acid | 1.0 | 1.1 |
| 1-Hydroxyethylidene-1,1-diphosphonic acid | 3.0 | 3.2 |
| Sodium sulfite | 4.0 | 4.4 |
| Potassium carbonate | 30.0 | 37.0 |
| Potassium bromide | 1.4 | 0.3 |
| Potassium iodide | 1.5 mg | — |
| Hydroxylamine sulfate | 2.4 | 2.8 |
| 4-[N-ethyl-N-(β-hydroxyethyl)amino]-2-methyl-aniline sulfate (P-5) | 4.5 | 6.2 |
| Water | ad1.0 l | 1.0 l |
| pH | 10.05 | 10.15 |
| (Bleaching bath) | | |
| Ferric sodium ethylenediaminetetraacetate trihydrate | 100.0 | 120.0 |
| Disodium ethylenediaminetetraacetate | 10.0 | 11.0 |
| 3-Mercapto-1,2,4-triazole | 0.08 | 0.09 |
| Ammonium bromide | 140.0 | 160.0 |
| Ammonium nitrate | 30.0 | 35.0 |
| Ammonia water (27%) | 6.5 ml | 4.0 ml |
| Water | ad1.0 l | ad1.0 l |
| pH | 6.0 | 5.7 |
| Fixing solution | | |
| Disodium ethylenediaminetetraacetate | 0.5 | 0.7 |
| Ammonium sulfite | 20.0 | 22.0 |
| Aqueous ammonium thiosulfate solution (700 g/l) | 290.0 ml | 320.0 ml |
| Water | ad1.0 l | ad1.0 l |
| pH | 6.7 | 7.0 |
| (Stabilizer) (common to the mother liquid and tank liquid) (unit: g) | | |
| Sodium p-toluenesulfinate | 0.03 | |
| Polyoxyethylene-p-monononylphenyl ether (average degree of polymerization: 10) | 0.2 | |
| Disodium ethylenediaminetetraacetate | 0.05 | |
| 1,2,4-Triazole | 1.3 | |
| 1,4-Bis(1,2,4-triazol-1-ylmethyl)piperazine | 0.75 | |
| Water | ad 1 l | |
| pH | 8.5 | |

The process in which the running processing solution was thus obtained will be referred to as "process 151". Then the same color developer as that described above was prepared except that the color developing agent P-5 contained therein was replaced with the equimolar amount to three mols of a color developing agent of the present invention given in Table 101, and the continuous process was conducted in the same manner as that described above to obtain running processing solutions (processes 152 to 159).

The graininess was determined by determining RMS of a film having an aperture diameter of 48 μm by an ordinary method and calculating the percentage thereof based on that of the process 151. RMS value of each sample was determined at a magenta density of "fog+0.4". The results are given in Table 101.

TABLE 101

| Process | Color developing agent | Amount of color developing agent *1) | Graininess | Remarks |
|---|---|---|---|---|
| 151 | P-5 | — | 100 | Comp. Ex. |
| 152 | D-1 | 3 mols | 90 | Present invention |
| 153 | D-2 | 2 mols | 89 | ditto |
| 154 | D-48 | 1 mol | 94 | ditto |
| 155 | D-49 | 1 mol | 92 | ditto |
| 156 | D-56 | 2 mols | 90 | ditto |
| 157 | D-67 | 2 mols | 90 | ditto |
| 158 | D-68 | 1 mol | 94 | ditto |
| 159 | D-88 | 1 mol | 91 | ditto |

*1) per mol of P-5 in process 151

It is apparent from Table 101 that the color developing agent of the present invention is more excellent than P-5 in the graininess. These excellent results obtained by the present inventors have not yet been expected in the prior art.

The 4-(N,N-dialkylamino)aniline derivatives of the present invention are new compounds which are useful as developing agents for silver halide color photography and, in addition, the use thereof as dyes and intermediates therefor, particularly intermediates for dyes for keratin fibers such as human hair, as medicines and intermediates therefor, and agricultural chemicals and intermediates therefor, is expected.

What is claimed is:

1. Aniline compounds of the following general formula (I):

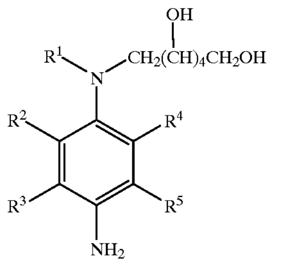

wherein $R^1$ represents an alkyl group, an aryl group or a heterocyclic group, $R^2$ to $R^5$ each represents a hydrogen atom or a substituent, and $R^2$ and $R^3$, $R^1$ and $R^2$, or $R^4$ and $R^5$ may form a ring together.

2. The Aniline compounds of claim 1 wherein $R^1$ represents a linear, branched or cyclic alkyl group having 1 to 25 carbon atoms, aryl group having 6 to 24 carbon atoms or five-membered or six-membered, saturated or unsaturated heterocyclic group containing 1 to 5 carbon atoms and at least one of oxygen, nitrogen and sulfur atoms, $R^2$ to $R^5$ each represents a hydrogen atom or a substituent, and $R^2$ and $R^3$, $R^1$ and $R^2$, or $R^4$ and $R^5$ may form a ring together.

3. The Aniline compounds of claim 2 wherein said substituent is selected from the group consisting of halogen atoms and an alkyl, aryl, heterocyclic, cyano, nitro, hydroxyl, carboxyl, sulfo, alkoxyl, aryloxy, acylamino, amino, alkylamino, anilino, ureido, sulfamoylamino, alkylthio, arylthio, alkoxycarbonylamino, sulfonamido, carbamoyl, sulfamoyl, sulfonyl, alkoxycarbonyl, heterocyclic oxy, azo, acyloxy, carbamoyloxy, silyl, silyloxy, aryloxycarbonylamino, imido, heterocyclic thio, sulfinyl, phosphonyl, aryloxycarbonyl and acyl groups.

4. The Aniline compounds of claim 3 wherein said substituent is selected from the group consisting of halogen atoms and a linear, branched or cyclic alkyl group having 1 to 25 carbon atoms, aryl group having 6 to 24 carbon atoms or five-membered or six-membered, saturated or unsaturated heterocyclic group containing 1 to 5 carbon atoms and at least one of oxygen, nitrogen and sulfur atoms, cyano, nitro, hydroxyl, carboxyl, sulfo, alkoxyl group having 1 to 16 carbon atoms, aryloxy group having 6 to 24 carbon atoms, acylamino group having 1 to 16 carbon atoms, amino, alkylamino group having 1 to 16 carbon atoms, anilino group having 6 to 24 carbon atoms, ureido group having 1 to 16 carbon atoms, sulfamoylamino group having 0 to 16 carbon atoms, alkylthio group having 1 to 16 carbon atoms, arylthio group having 6 to 24 carbon atoms, alkoxycarbonylamino group having 2 to 16 carbon atoms, sulfonamido group having 1 to 16 carbon atoms, carbamoyl group having 1 to 16 carbon atoms, sulfamoyl group having 0 to 16 carbon atoms, sulfonyl group having 1 to 16 carbon atoms, alkoxycarbonyl group having 1 to 16 carbon atoms, five-membered or six-membered, saturated or unsaturated heterocyclic oxy group containing 1 to 5 carbon atoms and at least one of oxygen, nitrogen and sulfur atoms, azo group having 1 to 16 carbon atoms, acyloxy group having 1 to 16 carbon atoms, carbamoyloxy group having 1 to 16 carbon atoms, silyl group having 3 to 16 carbon atoms, silyloxy group having 3 to 16 carbon atoms, aryloxycarbonylamino group having 7 to 24 carbon atoms, imido group having 4 to 16 carbon atoms, five-membered or six-membered, saturated or unsaturated heterocyclic thio group containing 1 to 5 carbon atoms and at least one of oxygen, nitrogen and sulfur atoms, sulfinyl group having 1 to 16 carbon atoms, phosphonyl group having 2 to 16 carbon atoms, aryloxycarbonyl group having 7 to 24 carbon atoms and acyl group having 1 to 16 carbon atoms.

5. The Aniline compounds of claim 4 wherein said ring formed by $R^2$ and $R^3$, $R^1$ and R2, or $R^4$ and $R^5$ is a five-membered or six-membered, saturated or unsaturated heterocyclic ring containing 1 to 5 carbon atoms and at least one of oxygen, nitrogen and sulfur atoms.

6. The Aniline compounds of claim 1 wherein $R^1$ is an alkyl group, $R^2$ and $R^4$ are hydrogen atom, alkyl groups or alkoxyl groups, $R^3$ is a hydrogen atom or a substituent and $R^5$ is alkyl groups or alkoxyl groups.

7. The Aniline compounds of claim 1 wherein $R^1$ is an alkyl group, $R^2$ is alkyl groups or alkoxyl groups, $R^3$ is a hydrogen atom or a substituent, $R^4$ is hydrogen atom, alkyl groups or alkoxyl groups, and $R^1$ and $R^2$ may form a ring together.

8. The Aniline compounds of claim 1 wherein $R^1$ is an alkyl group, $R^2$ is hydrogen atom, $R^3$ is a hydrogen atom or a substituent, $R^4$ is alkyl groups or alkoxyl groups, and $R^4$ and $R^5$ may form a ring together.

9. The Aniline compounds of claim 1 wherein $R^1$ represents an alkyl group having 1 to 15 carbon atoms, $R^3$ and $R^4$ each represents a hydrogen atom, and $R^5$ represents a hydrogen atom or an alkyl group having 1 to 25 carbon atoms, and $R^1$ and $R^2$ may form a substituted or unsubstituted ethylene chain or a substituted or unsubstituted trimethylene chain together.

10. A processing composition for color photography which contains at least one of the aniline compounds of the following general formula

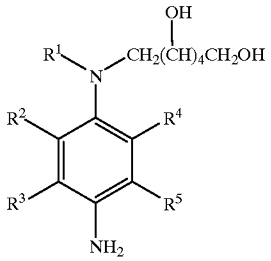

wherein $R^1$ represents an alkyl group, an aryl group or a heterocyclic group, $R^2$ to $R^5$ each represents a hydrogen atom or a substituent, and $R^2$ and $R^3$, $R^1$ and $R^2$, or $R^4$ and $R^5$ may form a ring together.

* * * * *